(12) United States Patent
Leak

(10) Patent No.: US 11,980,402 B2
(45) Date of Patent: May 14, 2024

(54) APPARATUS FOR STABILIZATION OF A BONE FRACTURE SITE

(71) Applicant: Leith Medical, LLC, Austin, TX (US)

(72) Inventor: Timothy Leak, Austin, TX (US)

(73) Assignee: LEITH MEDICAL, INC., Austin, TX (US)

( * ) Notice: Subject to any disclaimer, the term of this patent is extended or adjusted under 35 U.S.C. 154(b) by 143 days.

(21) Appl. No.: 17/068,900

(22) Filed: Oct. 13, 2020

(65) Prior Publication Data

US 2021/0106369 A1  Apr. 15, 2021

Related U.S. Application Data

(60) Provisional application No. 62/914,749, filed on Oct. 14, 2019.

(51) Int. Cl.
*A61B 17/84* (2006.01)
*A61B 17/86* (2006.01)
*A61B 17/88* (2006.01)

(52) U.S. Cl.
CPC ........ *A61B 17/842* (2013.01); *A61B 17/8695* (2013.01); *A61B 17/8869* (2013.01); *A61B 17/8897* (2013.01)

(58) Field of Classification Search
CPC ... A61B 17/842; A61B 17/82; A61B 17/8869; A61B 17/8861; A61B 17/8872
See application file for complete search history.

(56) References Cited

U.S. PATENT DOCUMENTS 5,370,646 A * 12/1994 Reese ................ A61B 17/8872
411/509
5,501,684 A   3/1996 Schlapfer
(Continued)

FOREIGN PATENT DOCUMENTS

WO   2007/056516 A2   5/2007
WO   2014/062690 A1   4/2014
(Continued)

OTHER PUBLICATIONS

International Search Report and Written Opinion of International Application No. PCT/US2020/055302, dated Feb. 10, 2021, 21 pages.
(Continued)

*Primary Examiner* — Amy R Sipp
(74) *Attorney, Agent, or Firm* — Slayden Grubert Beard PLLC

(57) ABSTRACT

An apparatus for stabilization of a bone fracture site, including a wire that is configured to be positioned through corresponding holes of a first bone and an adjacent second bone; and a tension washer coupled to a first end of the wire, the tension washer rotatable about the first end of the wire, wherein the wire is configured to be positioned through the corresponding holes of the first and the second bone, the tension washer is configured to be positioned proximate a first surface of the second bone, wherein the tension washer includes a first surface having a length longer than a diameter of the corresponding holes of the first and the second bones, wherein the tension washer is configured to rotate such that the first surface of the tension washer abuts the first surface of the second bone.

21 Claims, 31 Drawing Sheets

(56) References Cited

U.S. PATENT DOCUMENTS

| | | |
|---|---|---|
| 5,520,690 A | 5/1996 | Errico |
| 5,578,034 A | 11/1996 | Estes |
| 5,902,303 A | 5/1999 | Eckhof |
| 5,954,722 A | 9/1999 | Bono |
| 6,235,033 B1 | 5/2001 | Brace |
| 6,241,731 B1 | 6/2001 | Fiz |
| 6,261,291 B1 | 7/2001 | Talaber |
| 6,599,290 B2 | 7/2003 | Bailey |
| 6,602,255 B1 | 8/2003 | Campbell |
| 6,884,242 B2 | 4/2005 | LeHuec |
| 7,001,389 B1 | 2/2006 | Navarro |
| D603,510 S | 11/2009 | Kriska |
| 7,766,917 B2 | 8/2010 | Kugler |
| 7,766,947 B2 | 8/2010 | Hawkes |
| 7,963,982 B2 | 6/2011 | Kirschman |
| 7,981,140 B2 | 7/2011 | Burkhart |
| 8,012,174 B2 | 9/2011 | ElAttrache et al. |
| 8,100,955 B2 | 1/2012 | Blain |
| 8,202,296 B2 | 6/2012 | Burkhart |
| 8,202,297 B2 | 6/2012 | Burkhart |
| 8,231,653 B2 | 7/2012 | Dreyfuss |
| 8,348,975 B2 | 1/2013 | Dreyfuss |
| 8,388,665 B2 | 3/2013 | Eberlein |
| 8,465,522 B2 | 6/2013 | Burkhart |
| 8,506,607 B2 | 8/2013 | Eckhoff et al. |
| 8,562,656 B2 | 10/2013 | Humphreys |
| 8,591,578 B2 | 11/2013 | Albertorio et al. |
| 8,628,573 B2 | 1/2014 | Roller et al. |
| 8,663,279 B2 | 3/2014 | Burkhart et al. |
| 8,784,459 B2 | 7/2014 | Kaufman et al. |
| 8,858,560 B2 | 10/2014 | Bradley et al. |
| 8,961,569 B2 | 2/2015 | Kaufman et al. |
| 8,986,346 B2 | 3/2015 | Dreyfuss |
| 9,044,273 B2 | 6/2015 | Richelsoph |
| 9,107,653 B2 | 8/2015 | Sullivan |
| 9,113,859 B2 | 8/2015 | Dooney, Jr. et al. |
| 9,179,950 B2 | 11/2015 | Zajac et al. |
| 9,204,960 B2 | 12/2015 | Albertorio et al. |
| 9,326,844 B2 | 5/2016 | Schmieding et al. |
| 9,332,979 B2 | 5/2016 | Sullivan |
| 9,345,471 B2 | 5/2016 | Sullivan |
| 9,421,086 B2 | 8/2016 | Roller et al. |
| 9,463,011 B2 | 10/2016 | Dreyfuss et al. |
| 9,504,462 B2 | 11/2016 | Dooney, Jr. et al. |
| 9,526,489 B2 | 12/2016 | Burkhart |
| 9,615,821 B2 | 4/2017 | Sullivan |
| 9,642,610 B2 | 5/2017 | Albertorio et al. |
| 9,687,222 B2 | 6/2017 | Dreyfuss et al. |
| 9,693,765 B2 | 7/2017 | Sullivan et al. |
| 9,737,292 B2 | 8/2017 | Sullivan et al. |
| 9,801,621 B2 | 10/2017 | Benavitz |
| 9,855,029 B2 | 1/2018 | Sullivan |
| 9,867,607 B2 | 1/2018 | Sullivan |
| 9,913,672 B2 | 3/2018 | Kaufmann |
| 10,076,407 B2 | 9/2018 | Albertorio et al. |
| 10,085,739 B2 | 10/2018 | Dooney, Jr. et al. |
| 10,105,169 B2 | 10/2018 | Leak et al. |
| 10,172,606 B2 | 1/2019 | Sullivan et al. |
| 10,172,607 B2 | 1/2019 | Burkhart |
| 10,206,670 B2 | 2/2019 | Thornes |
| 10,245,016 B2 | 4/2019 | Zajac et al. |
| 10,251,686 B2 | 4/2019 | Zajac et al. |
| 10,265,060 B2 | 4/2019 | Dooney, Jr. et al. |
| 10,285,801 B2 | 5/2019 | Roller et al. |
| 10,335,136 B2 | 7/2019 | Dooney, Jr. et al. |
| 10,368,855 B2 | 8/2019 | Burkhart |
| 10,398,426 B2 | 9/2019 | Burkhart et al. |
| 10,441,408 B2 | 10/2019 | Dreyfuss et al. |
| 10,448,943 B2 | 10/2019 | Guerra et al. |
| 10,492,776 B2 | 12/2019 | Dreyfuss et al. |
| RE47,811 E | 1/2020 | Sullivan et al. |
| 10,524,775 B2 | 1/2020 | Benedict et al. |
| 10,568,733 B2 | 2/2020 | Park et al. |
| 10,575,842 B2 | 3/2020 | Lund |
| 10,646,327 B2 | 5/2020 | Lund |
| 10,736,620 B2 | 8/2020 | Dreyfuss et al. |
| 10,736,679 B2 | 8/2020 | Leak et al. |
| 2001/0047172 A1 | 11/2001 | Foley |
| 2002/0019634 A1* | 2/2002 | Bonutti ............... A61B 17/82 606/57 |
| 2002/0188297 A1* | 12/2002 | Dakin ............... A61B 17/842 606/103 |
| 2003/0225409 A1 | 12/2003 | Freid |
| 2004/0019353 A1 | 1/2004 | Freid |
| 2004/0127900 A1 | 7/2004 | Konieczynski |
| 2006/0009770 A1 | 1/2006 | Speirs |
| 2006/0264944 A1* | 11/2006 | Cole ............... A61B 17/725 606/62 |
| 2007/0244489 A1 | 10/2007 | Patel |
| 2008/0147127 A1* | 6/2008 | Tipirneni ............ A61B 17/864 606/301 |
| 2008/0287999 A1 | 11/2008 | Markworth |
| 2011/0034925 A1 | 2/2011 | Tipirneni |
| 2011/0172666 A1 | 7/2011 | Heilman |
| 2013/0123841 A1* | 5/2013 | Lyon ............... A61B 17/0401 606/232 |
| 2013/0190825 A1 | 7/2013 | Perrow |
| 2015/0094764 A1 | 4/2015 | Konieczynski |
| 2015/0245859 A1 | 9/2015 | McMillen |
| 2015/0359574 A1 | 12/2015 | Black |
| 2016/0081730 A1 | 3/2016 | Black et al. |
| 2016/0213368 A1 | 7/2016 | Stecco |
| 2016/0220286 A1 | 8/2016 | Garvey et al. |
| 2016/0317203 A1 | 11/2016 | Weiman et al. |
| 2016/0317318 A1 | 11/2016 | Carlson et al. |
| 2017/0209140 A1 | 4/2017 | Thornes |
| 2017/0156767 A1 | 6/2017 | Chaudot et al. |
| 2017/0156771 A1 | 6/2017 | Brinker |
| 2019/0133655 A1 | 5/2019 | Bonutti |
| 2020/0330140 A1 | 10/2020 | Leak et al. |
| 2021/0106367 A1 | 4/2021 | Leak |

FOREIGN PATENT DOCUMENTS

| | | |
|---|---|---|
| WO | 2014/089534 A2 | 6/2014 |
| WO | 2016/070191 A1 | 5/2016 |
| WO | 2017/196769 A1 | 11/2017 |

OTHER PUBLICATIONS

International Search Report and Written Opinion of International Application No. PCT/US2020/055303, dated Feb. 19, 2021, 21 pages.

International Preliminary Report of International Application No. PCT/US2020/055303, dated Apr. 28, 2022, 10 pages.

International Preliminary Report and Written Opinion of International Application No. PCT/US2020/055302, dated Apr. 28, 2022, 9 pages.

* cited by examiner

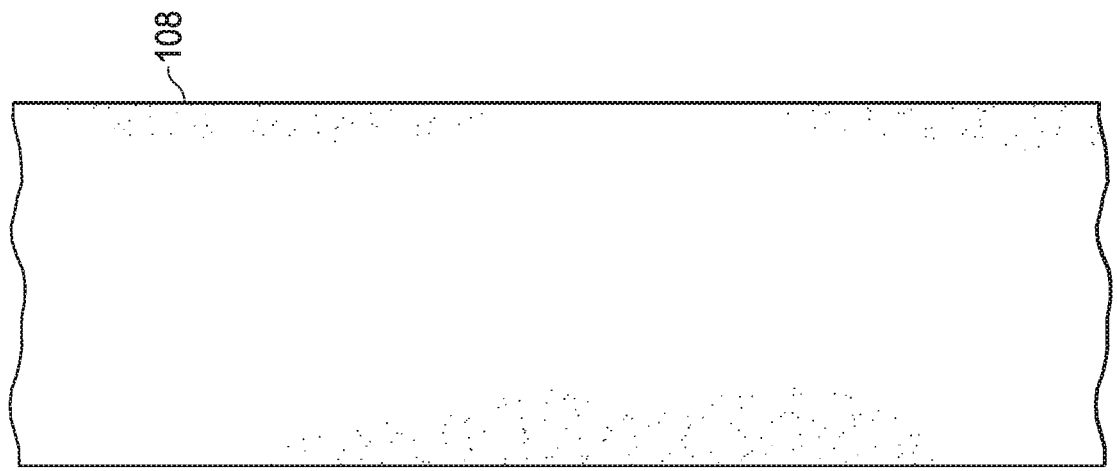
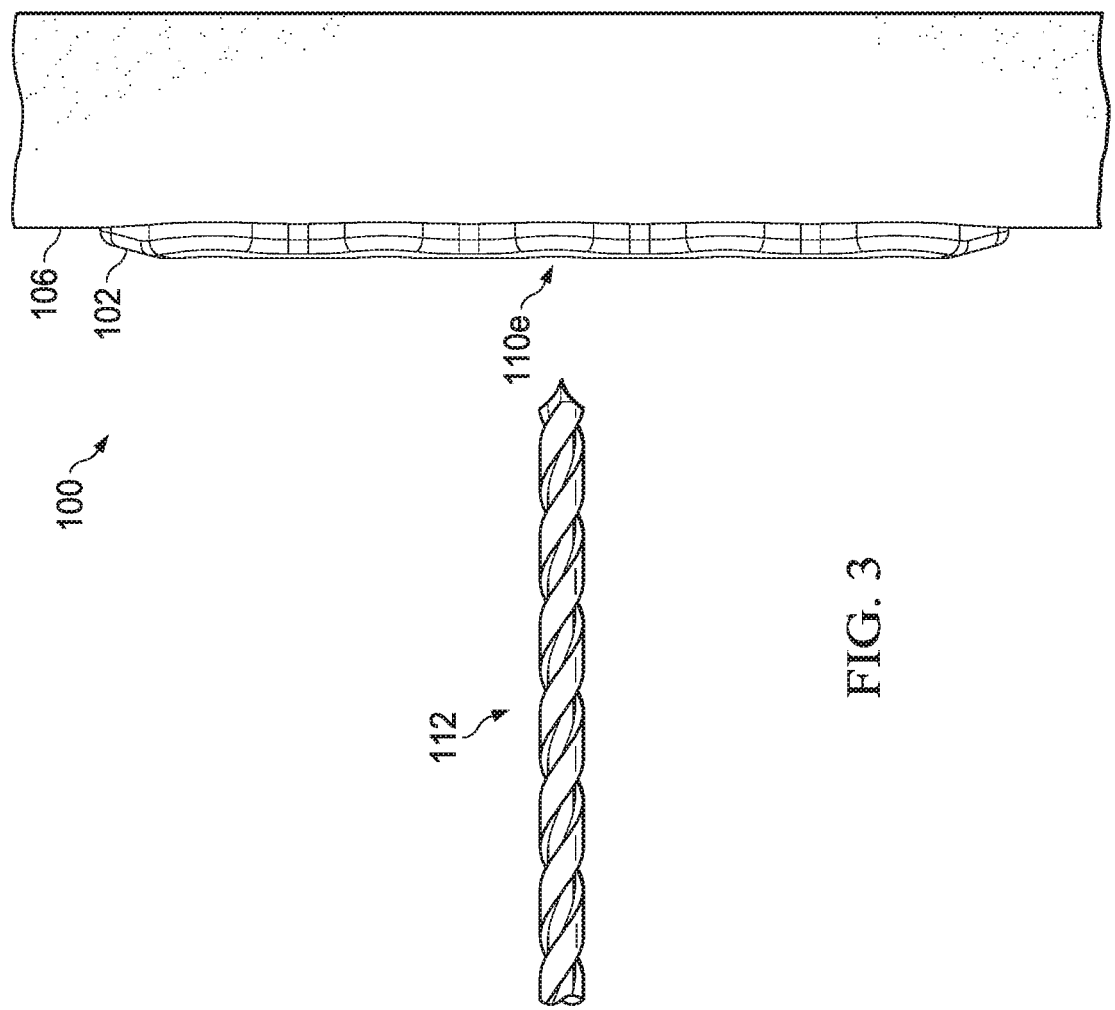
FIG. 3

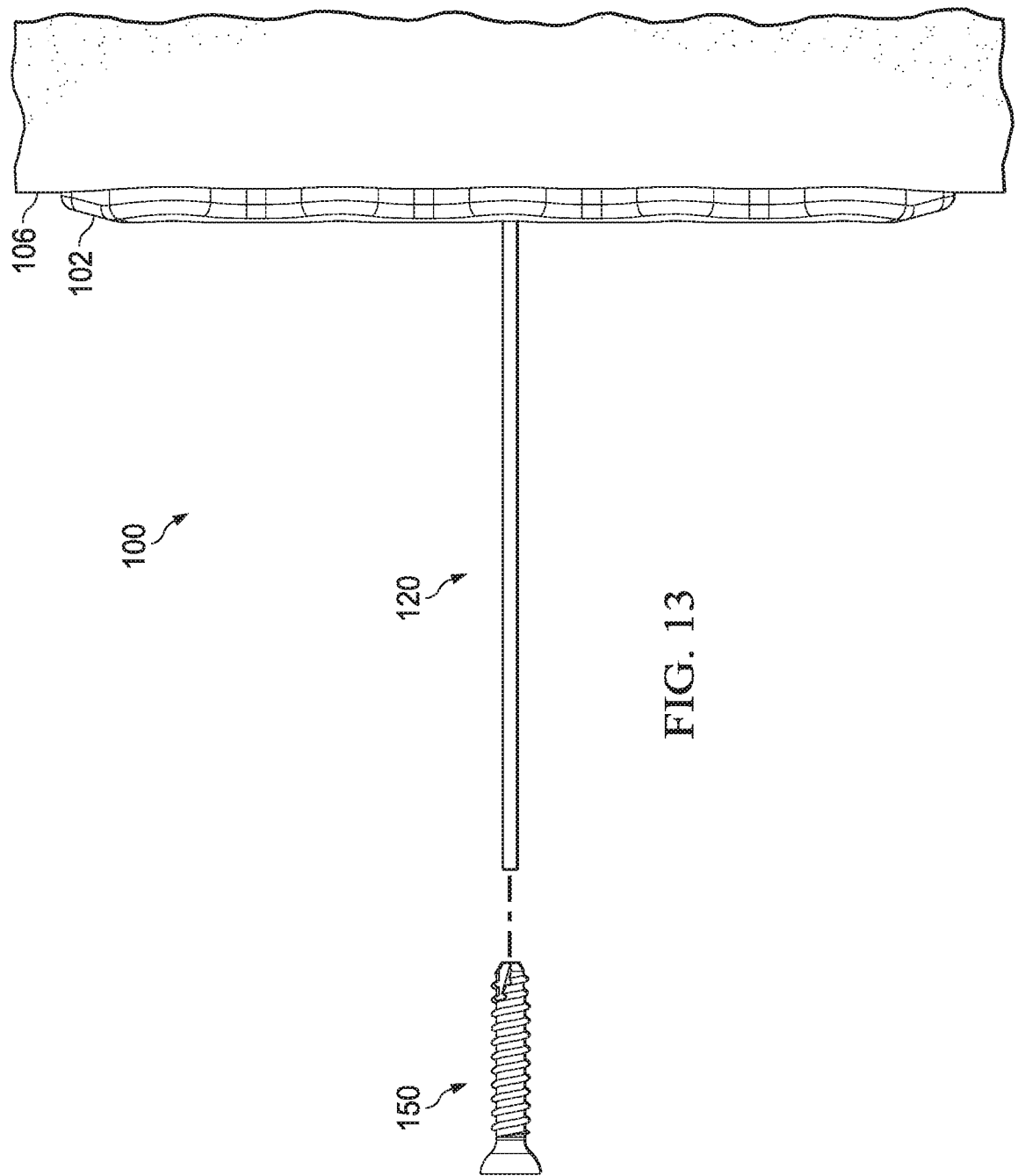

APPARATUS FOR STABILIZATION OF A BONE FRACTURE SITE

RELATED APPLICATIONS

This application claims the benefit of U.S. Provisional Application 62/914,749 filed Oct. 14, 2019.

BACKGROUND

Field of the Disclosure

The disclosure relates generally to an apparatus for stabilization of a bone, and specifically, stabilization of a bone fracture site.

Description of the Related Art

For various bone fractures, the use of orthopedic plates is a technique to stabilize the bone as needed for proper healing. Generally, a rigid, often metal plate is placed on the outer surface of the bone across the fracture, and orthopedic screws extend through the plate into the bone on either side of the fracture. The plate offers support and stability to the bone during the healing period.

SUMMARY

Innovative aspects of the subject matter described in this specification may be embodied in an apparatus for stabilization of a bone fracture site, including: a bone fixation plate including a plurality of fastener holes, wherein the bone fixation plate is configured to be coupled to a first bone with one or more fasteners positioned through respective fastener holes of the plurality of fastener holes; a wire including i) a smooth portion and ii) a toothed portion; a tension washer coupled to a first end of the wire, the tension washer rotatable about the first end of the wire, the wire configured to be positioned through a particular fastener hole of the bone fixation plate and through corresponding holes of the first bone and an adjacent second bone such that the tension washer is positioned proximate a first surface of the second bone opposite a surface of the first bone adjacent the bone fixation plate; a tension washer positioner including an angled tip, the tension washer positioner configured to be positioned through the particular fastener hole of the bone fixation plate and through the corresponding holes of the first and the second bones to adjust an angle of the tension washer with respect to the tension washer; a cannulated screw configured to be inserted over the wire and through the particular fastener hole; and a lock washer configured to be inserted over the wire and positioned between two adjacent teeth of the toothed portion of the wire adjacent the hollow screw to couple the wire to the bone fixation plate.

These and other embodiments may each optionally include one or more of the following features. For instance, a tensioner configured to position the lock washer between the two adjacent recesses of the toothed portion of the wire. The one or more fasteners positioned through the respective fastener holes of the plurality of fastener holes are further coupled within the first bone to couple the bone fixation plate to the first bone. The tension washer positioner is cannulated such that the tension washer positioner is configured to be inserted over the wire. The tension washer includes a first surface having a length longer than a diameter of the corresponding holes of the first and the second bones, wherein the tension washer is configured to rotate such that when the lock washer is positioned between the two adjacent teeth of the teethed portion of the wire, the first surface of the tension washer abuts the first surface of the second bone. The first surface of the tension washer may have an angle of approximately 90 degrees with respect to the wire when the first surface of the tension washer is configured to abut the first surface of the second bone. A width of the tension washer is less than a diameter of the corresponding holes of the first and the second bones. The tension washer positioner is configured to adjust the angle of the tension washer with respect to the tension wire to be substantially the same as an angle of the angled tip of the tension washer positioner. The first bone may be a tibia, and the second bone may be a fibula. The tension washer is configured to have a rotation with respect to the wire when positioned through the particular fastener hole of the bone fixation plate and the corresponding holes of the first bone. The rotation may be approximately 15 degrees. The lock washer includes one or more teeth and one or more recesses between adjacent teeth, wherein when the lock washer is coupled to a particular tooth between adjacent recesses of the toothed portion of the wire, the teeth of the lock washer are configured to prevent movement of the lock washer to a second end of the wire opposite the first end of the wire.

Innovative aspects of the subject matter described in this specification may be embodied in an apparatus including a wire configured to be positioned through corresponding holes of a first bone and an adjacent second bone; and a tension washer rotatably coupled to a first end of the wire, and configured to be positioned proximate a first surface of the second bone, wherein the tension washer includes a first surface having a length longer than a diameter of the corresponding holes of the first and the second bones, wherein the tension washer is configured to rotate about the first end of the wire such that the first surface of the tension washer abuts the first surface of the second bone.

These and other embodiments may each optionally include one or more of the following features. For instance, the tension washer is configured to have a range of rotation about the first end of the wire such that the tension washer forms an angle with respect to the wire. The tension washer is configured to have an angle of approximately 90 degrees with respect to the wire when the first surface of the tension washer is placed to abut the first surface of the second bone. The tension washer is configured to have an angle of approximately 0 to 15 degrees with respect to the wire when passing through the corresponding holes of the first and the second bones. A width of the first surface of the tension washer is less than the length of the first surface of the tension washer. The first bone may be a tibia, and the second bone may be a fibula. The tension washer rotatably may be coupled to the first end of the wire by a pin.

Innovative aspects of the subject matter described in this specification may be embodied in an apparatus for stabilization of a bone fracture site, including a cannulated tension washer positioner including an angled tip, the tension washer positioner configured to be positioned over a wire positioned through corresponding holes of a first bone and an adjacent second bone, the cannulated tension washer positioner configured to adjust an angle of a rotatable tension washer coupled to a first end of the wire, the wire positioned through the corresponding holes of the first and the second bone and the tension washer positioned adjacent a first surface of the second bone.

The details of one or more embodiments of the subject matter described in this specification are set forth in the accompanying drawings and the description below. Other

BRIEF DESCRIPTION OF DRAWINGS

FIG. 3 illustrates a side view of the apparatus prior to creation of corresponding holes within the first bone and a second bone.

FIGS. 13-14 illustrate a side view of the apparatus including a cannulated screw.

DESCRIPTION OF PARTICULAR EMBODIMENT(S)

Figure 1A:
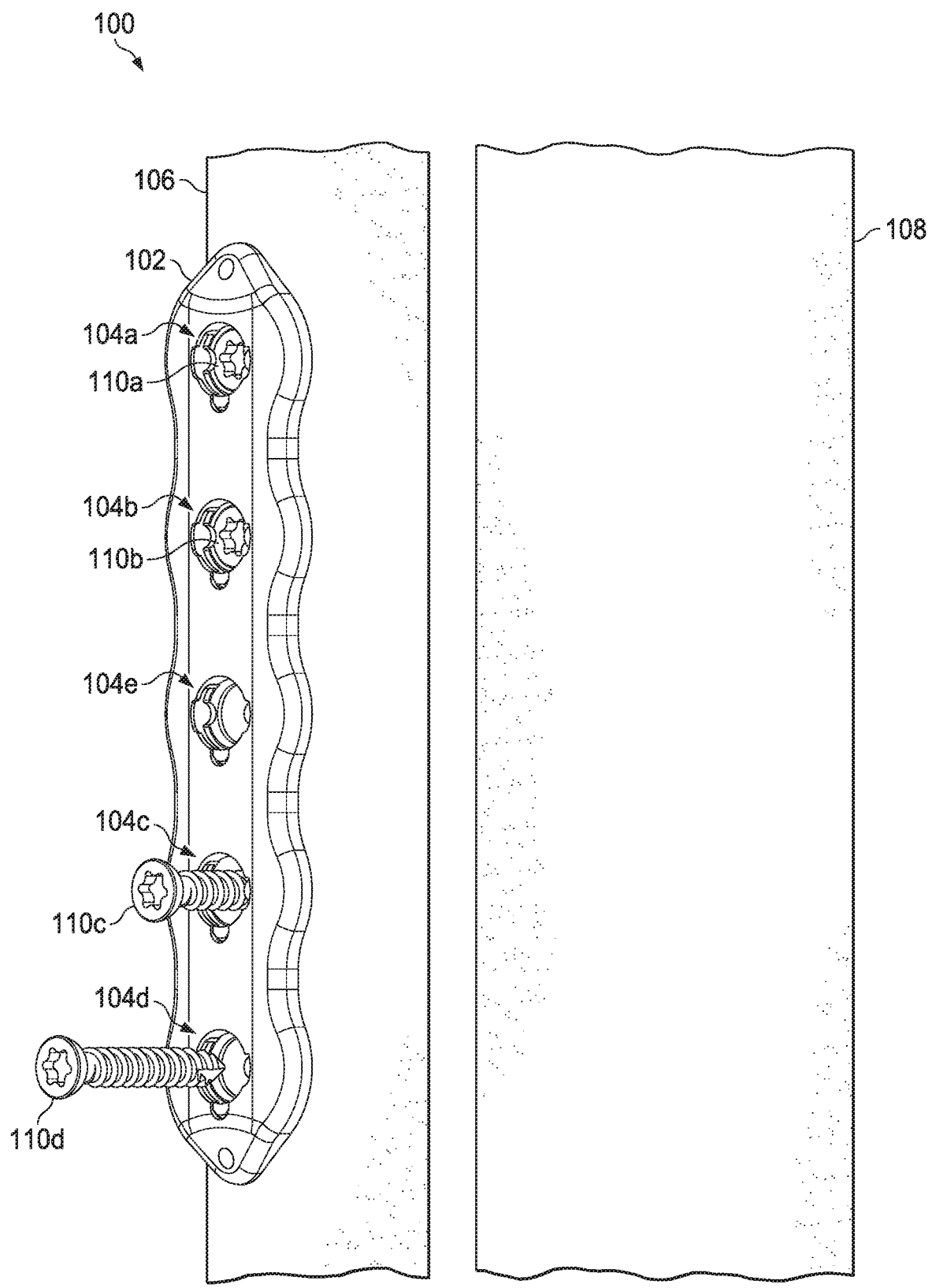
FIG. 1A illustrates a perspective view of an apparatus for stabilization of a bone fracture site.
Figure 1B:
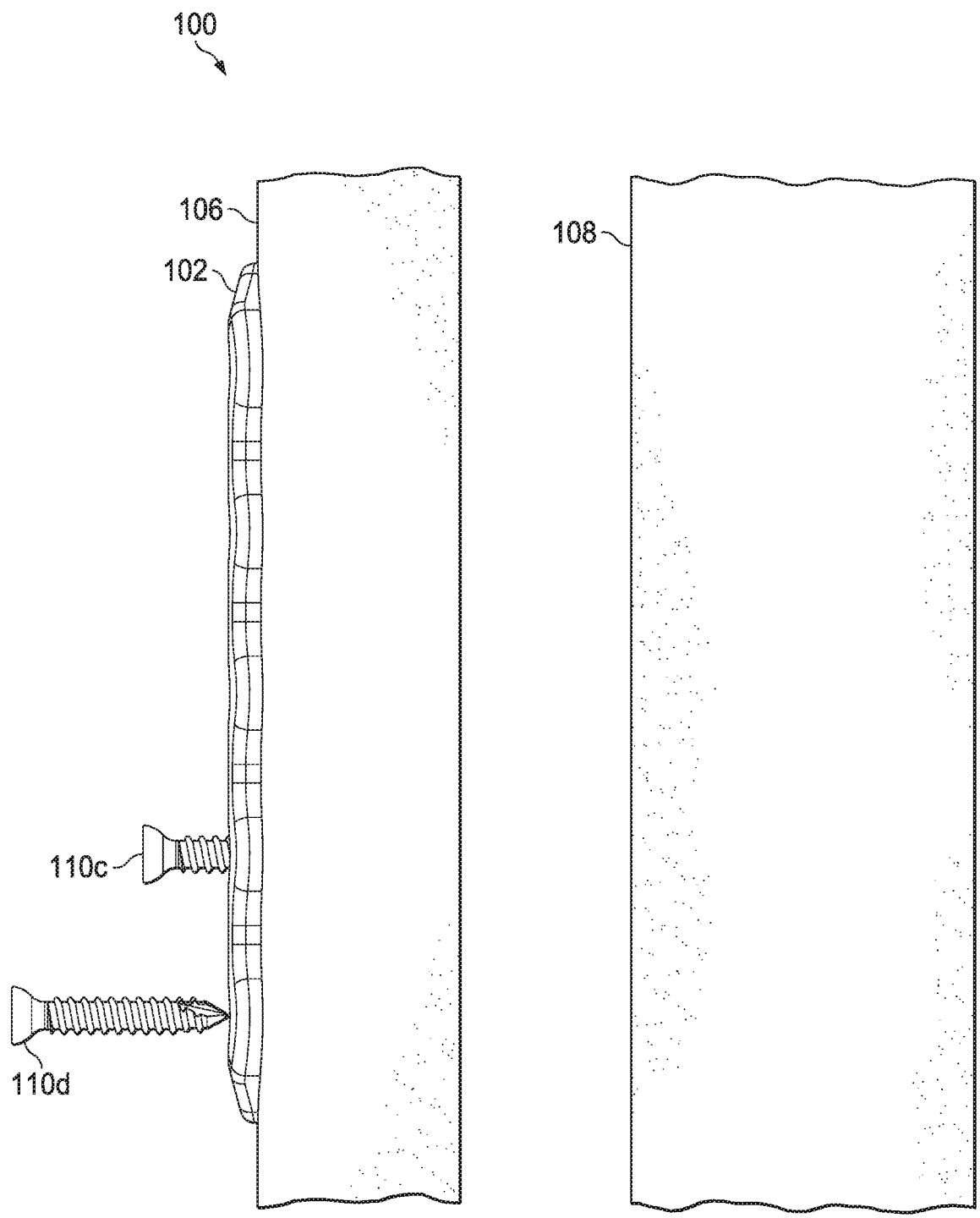
FIG. 1B illustrates a side view of the apparatus for stabilization of a bone fracture site.

FIG. 1A illustrates a perspective view of an apparatus 100 for stabilization of a bone fracture site; and FIG. 1B illustrates a side view of the apparatus 100. Specifically, the apparatus 100 includes a bone fixation plate 102 that includes a plurality of fastener holes 104a, 104b, 104c, 104d, 104e (collectively referred to as fastener holes 104). As shown, the bone fixation plate 102 can include five fastener holes 104; however, the bone fixation plate 102 can include any number of fastener holes 104. The bone fixation plate 102 can be coupled to a first bone 106. The first bone 106 can be proximate to a second bone 108. In some examples, the first bone 106 can include a tibia bone, and the second bone 108 can include a fibula bone. However, the first bone 106 and the second bone 108 can be any two proximate bones. For example, the apparatus 100 can be used in stabilization of a bone fracture site such as a hip fracture site, a clavicle fracture site, a chest cavity fracture site, a midfoot fracture site, a toe fusion, among other bone fracture sites. The bone fixation plate 102 can be coupled to the first bone 106 with fasteners 110a, 110b, 110c, 110d (collectively referred to as fasteners 110). The fasteners 110 can be positioned through respective fastener holes 104. That is, at least a portion of the fasteners 110 can be positioned through the respective fastener holes 104—for example, a threaded portion can be positioned through the respective fastener holes 104. As illustrated, the fasteners 110a, 110b, 110c, 110d are positioned through fastener holes 104a, 104b, 104c, 104d, respectively. However, a subset of the fasteners 110 can be positioned through a subset of respective fastener holes 104.

Figure 2A:
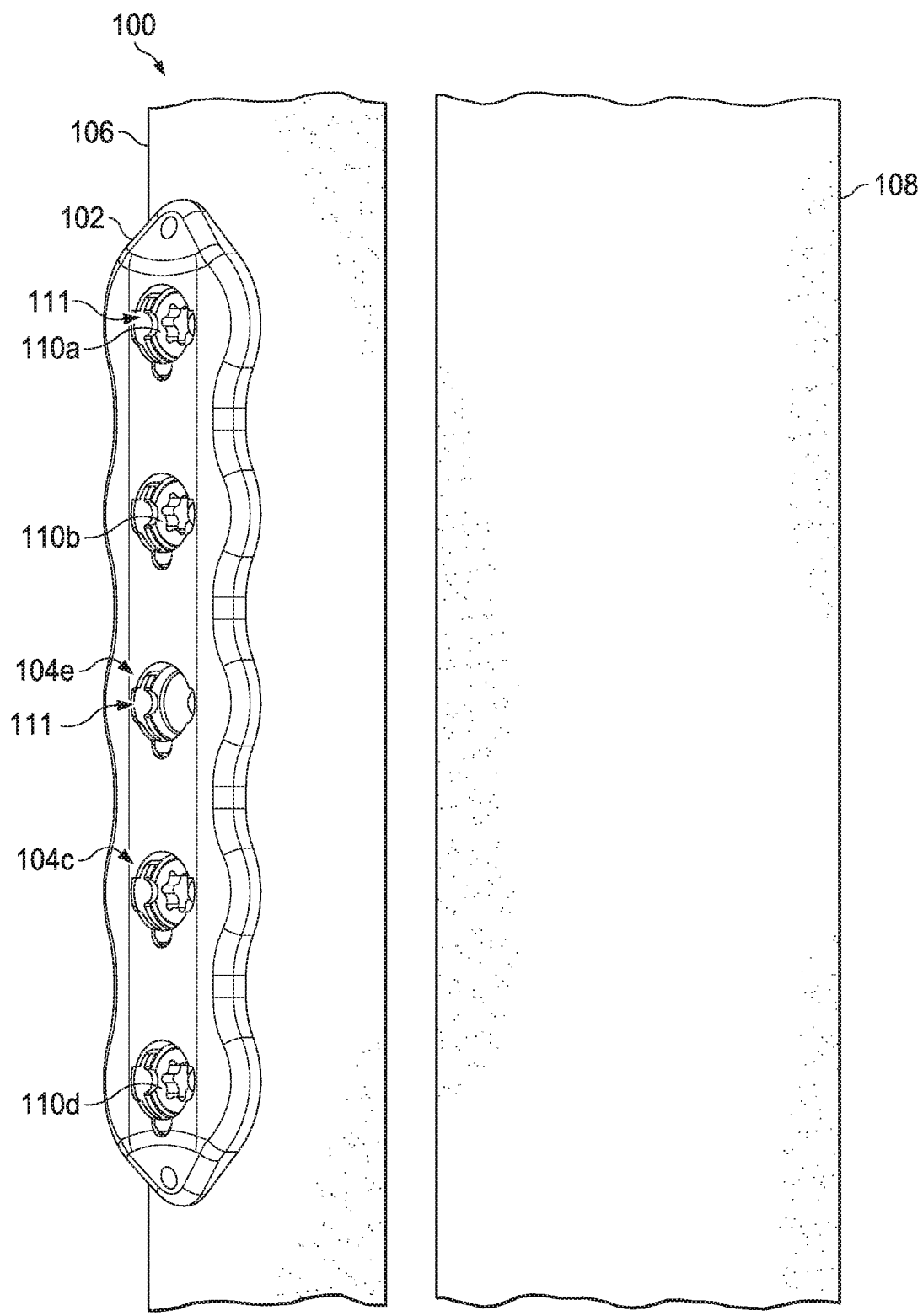
FIG. 2A illustrates a perspective view of the apparatus after coupling of a bone fixation plate to a first bone.
Figure 2B:
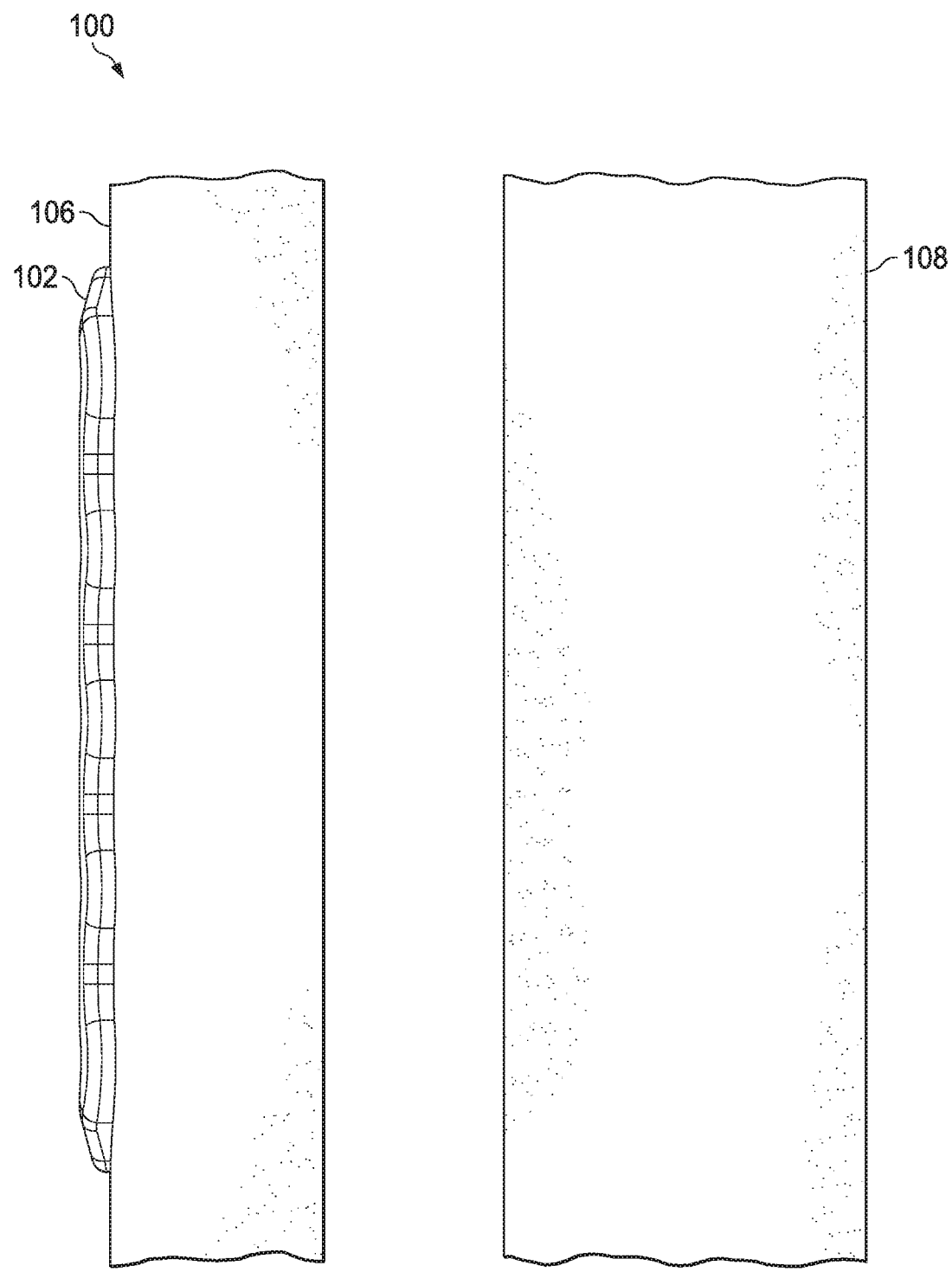
FIG. 2B is a side view of the apparatus after coupling of the bone fixation plate to the first bone.

FIG. 2A illustrates a perspective view of the apparatus 100 after coupling of the bone fixation plate 102 to the first bone 106; and FIG. 2B is a side view of the apparatus 100 after coupling of the bone fixation plate 102 to the first bone 106. As shown, a fastener 110 is not positioned through the fastener hole 104e; however, any of the fastener holes 104 can be independent of (i.e., not include) a corresponding fastener 110. To that end, as shown, the fasteners 110a, 110b, 110c, 110d are coupled within the first bone 106 to couple the bone fixation plate 102 to the first bone 106 (for example, the bone fixation plate 102 can be flush against the first bone 106).

In some examples, one or more of the fastener holes 104 can include one or more tabs 111. The tabs 111 can facilitate maintaining a positioning of the fasteners 110 once the fasteners are coupled within the first bone 106. In some examples, the tabs 111 are at least partially retractable within the bone fixation plate 102. When the tabs 111 are retracted within the bone fixation plate 102, an entirety of the fastener holes 104 may be unobstructed. In some examples, the tabs 111 are retracted when in contact with the fasteners 110—for example, when the fasteners 110 are inserted through the fastener holes 104. Once the fasteners 104 are coupled to the first bone 106, a head of the fastener 110 can be positioned between the tabs 111 and the first bone 106 such that the tabs 111 maintain the position of the respective fastener 110 (for example, maintains the coupling of the fastener 110 and the first bone 106). As the fastener 110 translates towards the first bone 106 (for example, as the fastener is "screwed into" the first bone 106), the tabs 111 can move outward (from previously being retracted) such that the head of the fastener 110 can be positioned between the tabs 111 and the first bone 106.

Figure 4:
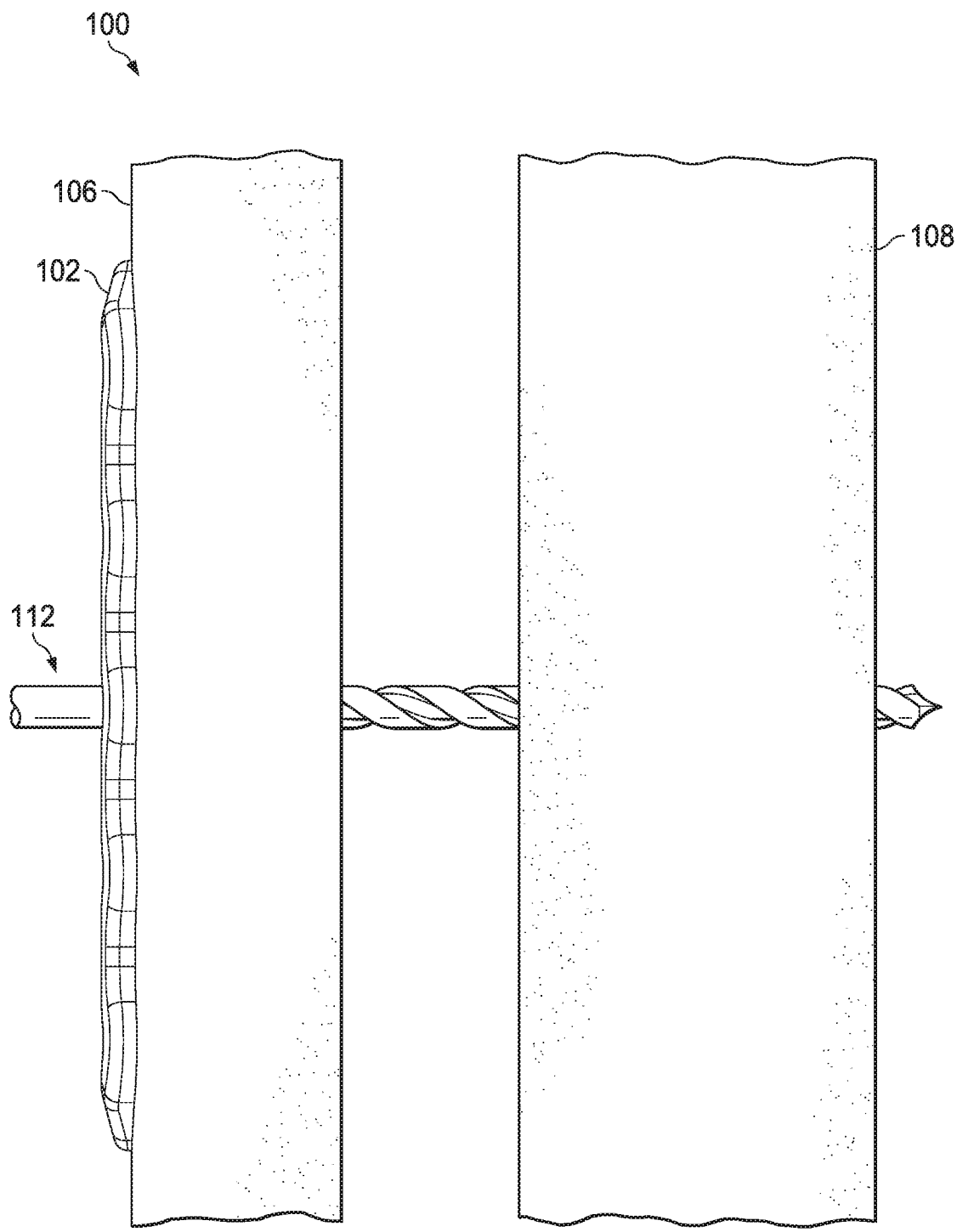
FIG. 4 illustrates a drilling apparatus inserted through a fastener hole, and through corresponding portions of the first bone and the second bone.

FIG. 3 illustrates a side view of the apparatus 100 prior to creation of corresponding holes within the first bone 106 and the second bone 108. For example, a drilling apparatus 112 (for example, a drill bit) can be inserted through the fastener hole 110e, and through corresponding portions of the first bone 106 and the second bone 108, as shown in FIG. 4. In some examples, the drilling apparatus 112 can be substantially perpendicular to the bone fixation plate 102 such that the corresponding holes of the first bone 106 and the second bone 108 generated by the drilling apparatus 112 can be substantially aligned. In some examples, the drilling apparatus 112 can be at an angle with respect to the bone fixation plate 102 such that the corresponding holes of the first bone 106 and the second bone 108 generated by the drilling apparatus are offset (for example, based on the angle of the drilling apparatus 112 with respect to the bone fixation plate 102).

Figure 5:
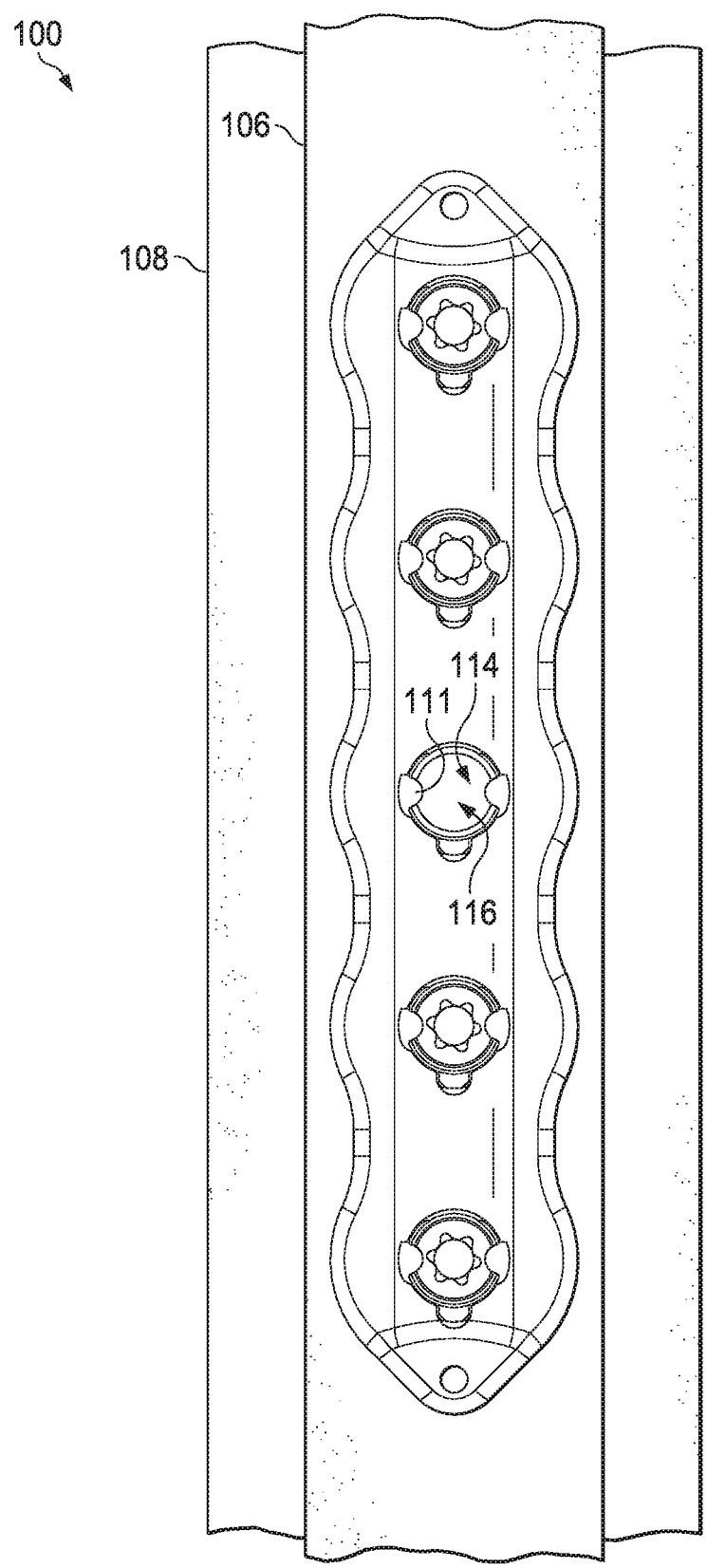
FIG. 5 illustrates a front view of the apparatus subsequent to creation of the corresponding holes within the first bone and the second bone.

FIG. 5 illustrates a front view of the apparatus 100 subsequent to creation of the corresponding holes within the first bone 106 and the second bone 108 (for example, removal of the drilling apparatus 112). To that end, the drilling apparatus 112 can create a first hole 114 within the first bone 106 and a second hole 116 within the second bone 108 (with first hole 114 in superimposition with the second hole 116 as viewed from the front view of the apparatus 100 of FIG. 5). In some examples, the first and the second holes 114, 116 have a diameter. In some examples, the diameter of the first and the second holes 114, 116 can be the diameter of the first and the second holes 114, 116 when the tabs 111 of the fastener holes 104 are retracted (for example, the first and the second holes 114, 116 are unobstructed).

Figure 6:
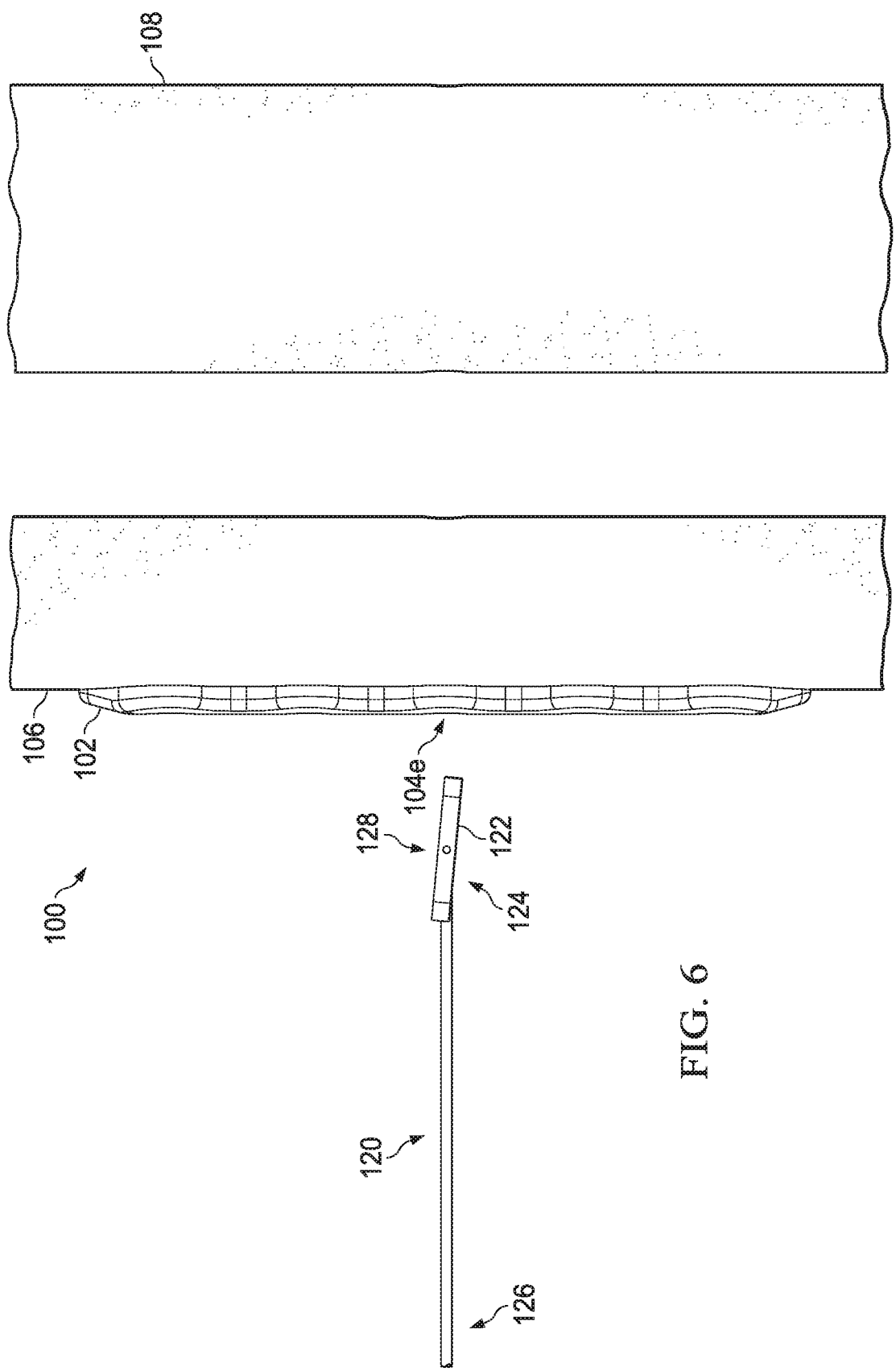
FIG. 6 illustrates a side view of the apparatus including a wire and a tension washer.

FIG. 6 illustrates a side view of the apparatus 100 including a wire 120 and a tension washer 122. The wire 120 and the tension washer 122 can be configured to be positioned through the fastener hole 104e, and the first and the second holes 114, 116 of the first and the second bones 106, 108, described further herein. The tension washer 122 can be coupled to a first end 124 of the wire 120, opposite a second end 126 of the wire 120. The tension washer 122 can be coupled to the first end 124 of the wire 120 about a pivot point 128. Specifically, a pin can be coupled through the tension washer 122 and the wire 120 to couple the tension washer 122 to the wire 120, and for the tension washer 122 to rotate about the pivot point 128.

Figure 7:
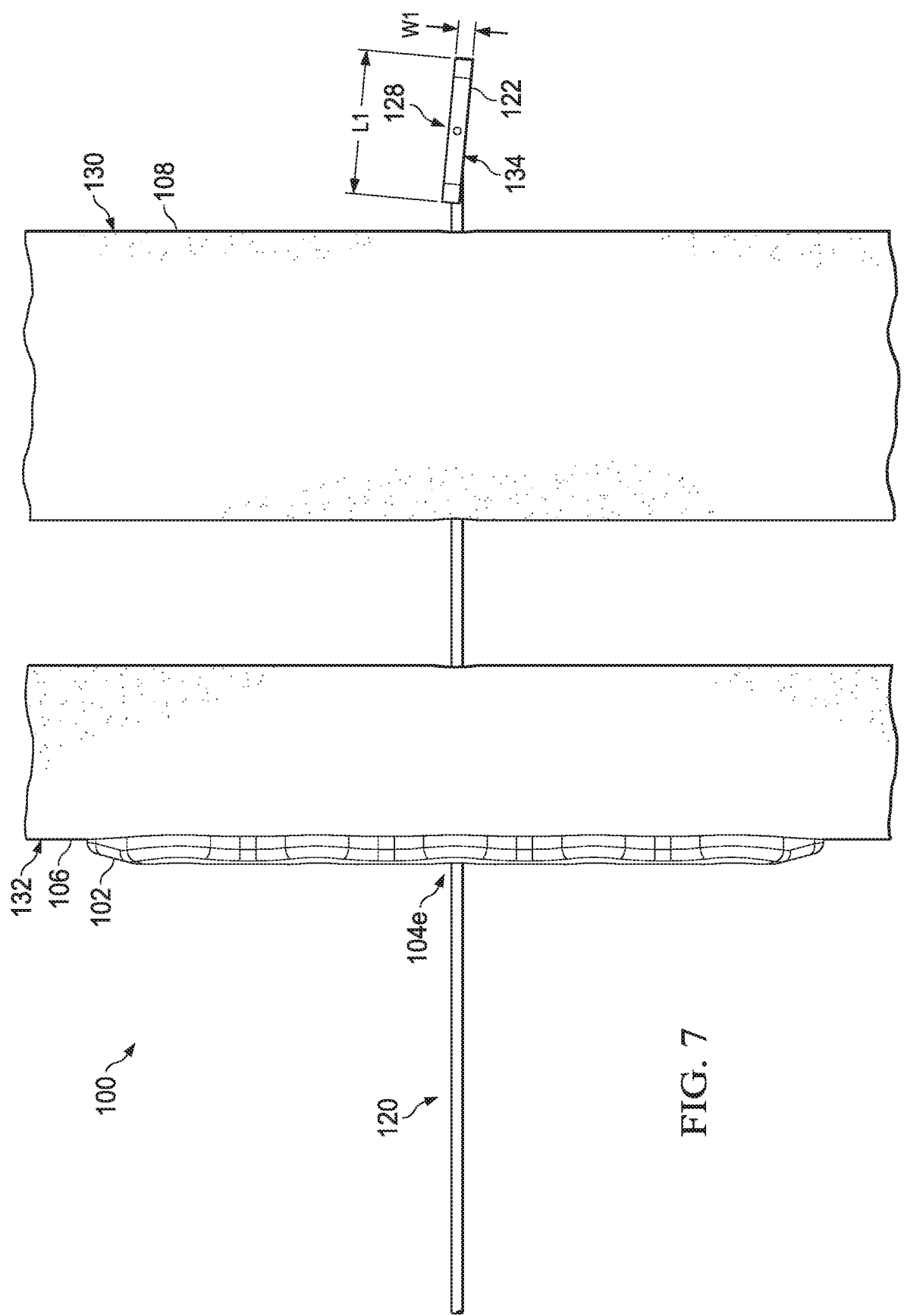
FIG. 7 illustrates a side view of the apparatus after positioning the wire and the tension washer through the fastener hole, and the first and the second holes of the first and the second bones.

FIG. 7 illustrates a side view of the apparatus 100 after positioning the wire 120 and the tension washer 122 through the fastener hole 104e, and the first and the second holes 114, 116 of the first and the second bones 106, 108. Specifically, the wire 120 can be configured to positioned through the fastener hole 104e, and the first and the second holes 114, 116 of the first and the second bones 106, 108 such that the tension washer 122 is positioned proximate a first surface 130 of the second bone 108. The first surface 130 can be opposite a surface 132 of the first bone 106 that is adjacent to the bone fixation plate 102. In some examples, the tension washer 122 can include a first surface 134 that has a length L1 that is longer than the diameter of the holes 114, 116 of the first and the second bones 106, 108. In some examples, a width W1 of the tension washer 122 can be less than the diameter of the holes 114, 116 of the first and the second bones 106, 108. In some examples, the tension washer 122 can be configured to be rotated with respect to the wire 120 about the pivot point 128 when positioned through the fastener hole 104e, and the first and the second holes 114, 116 of the first and the second bones 106, 108. That is, the tension washer 122 can be not substantially parallel with the wire 120 when the tension washer 122 is being positioned through the fastener hole 104e, and the first and the second holes 114, 116 of the first and the second bones 106, 108. In some examples, the tension washer 122 can be configured to have a rotation between approximately 0 to 15 degrees about the pivot point 128 with respect to the wire 120 when positioned through the fastener hole 104e, and the first and the second holes 114, 116 of the first and the second bones 106, 108.

Figure 8:
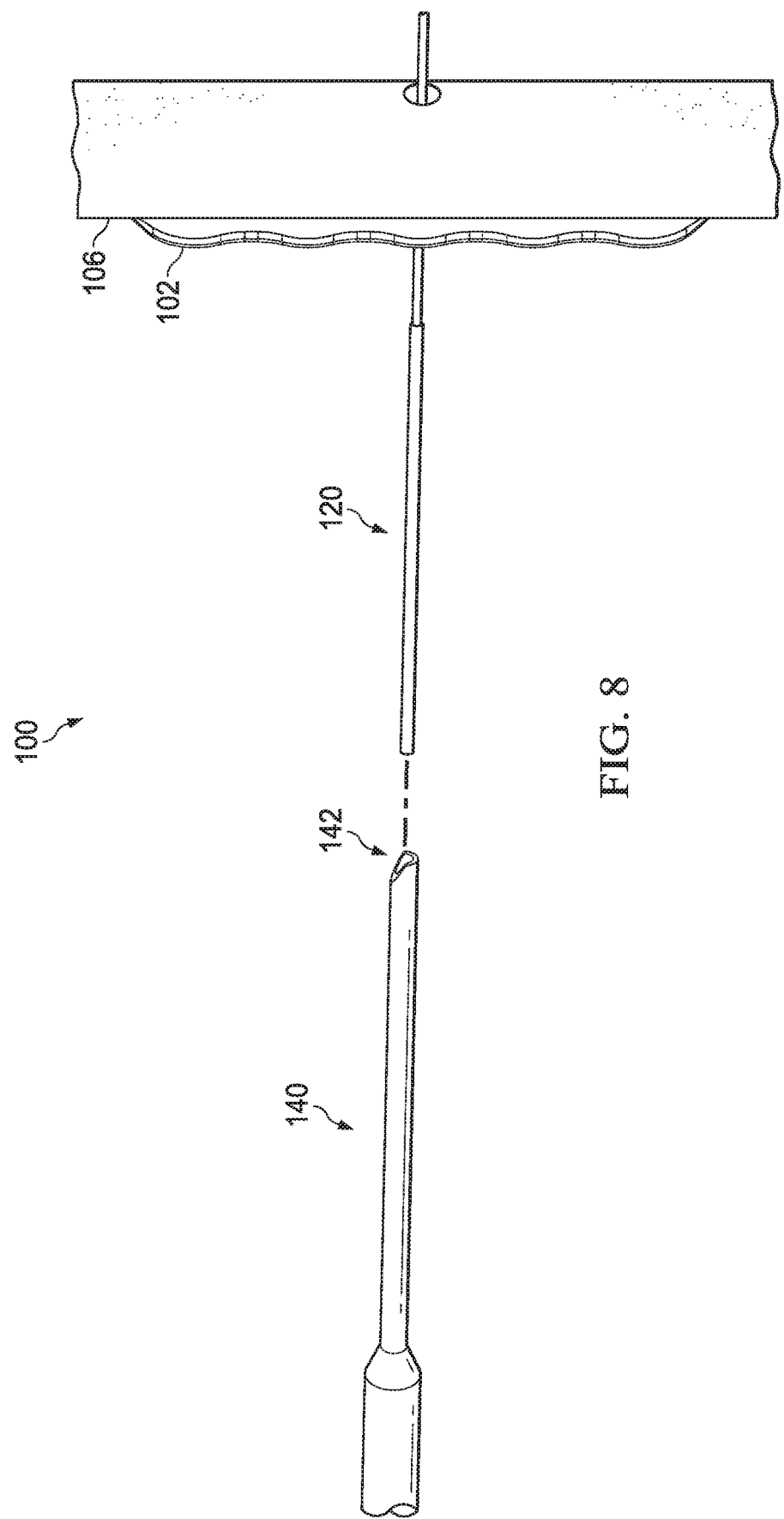
FIG. 8 illustrates a side view of the apparatus including a tension washer positioner.

FIG. 8 illustrates a side view of the apparatus 100 including a tension washer positioner 140. The tension washer positioner 140 can include an angled tip 142. The tension washer positioner 140 can be cannulated such that the tension washer positioner 140 can be inserted over the wire 120.

Figure 9:
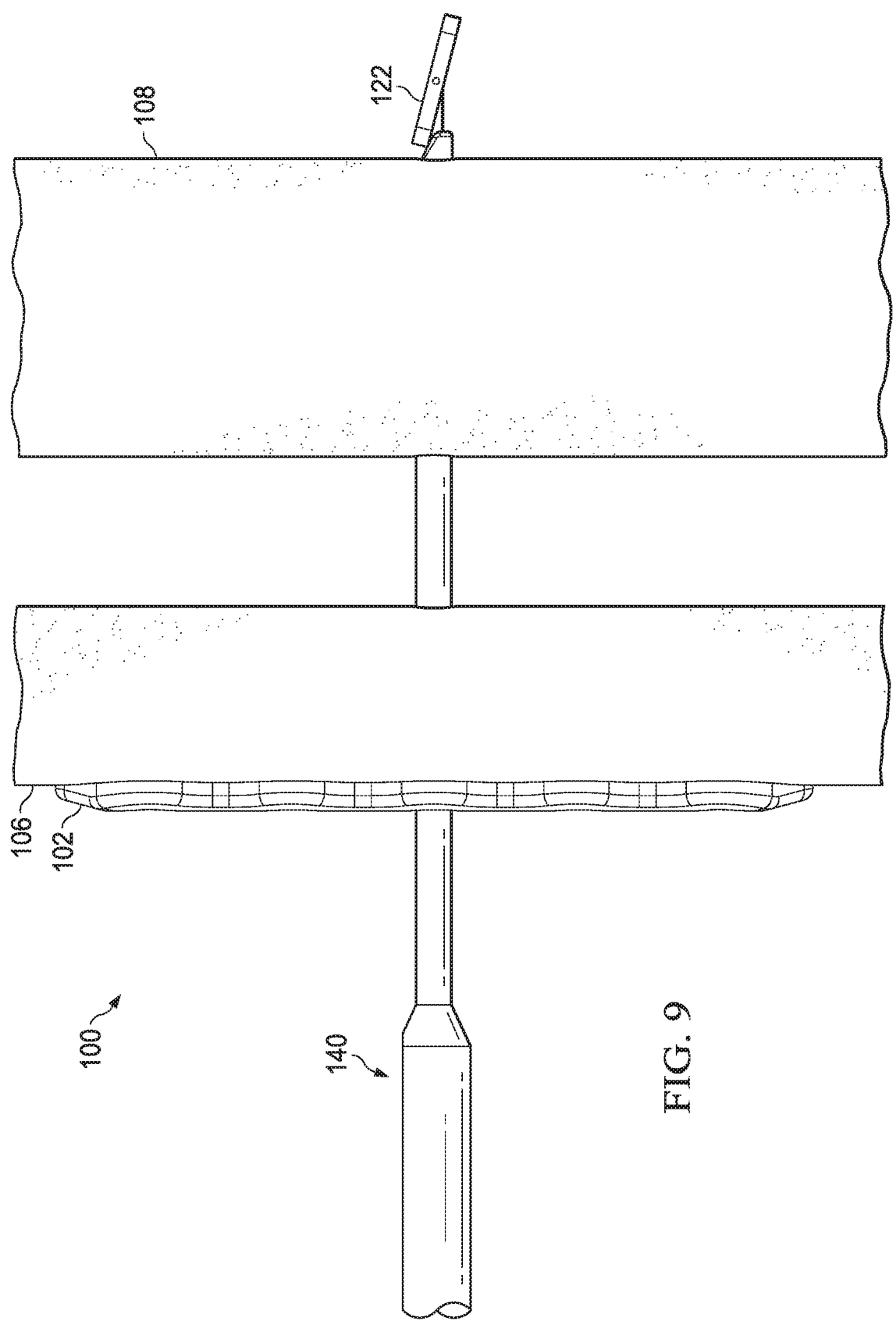
FIG. 9 illustrates a side view of the apparatus after the tension washer positioner has been positioned through the fastener hole, and the first and the second holes of the first and the second bones.
Figure 10:
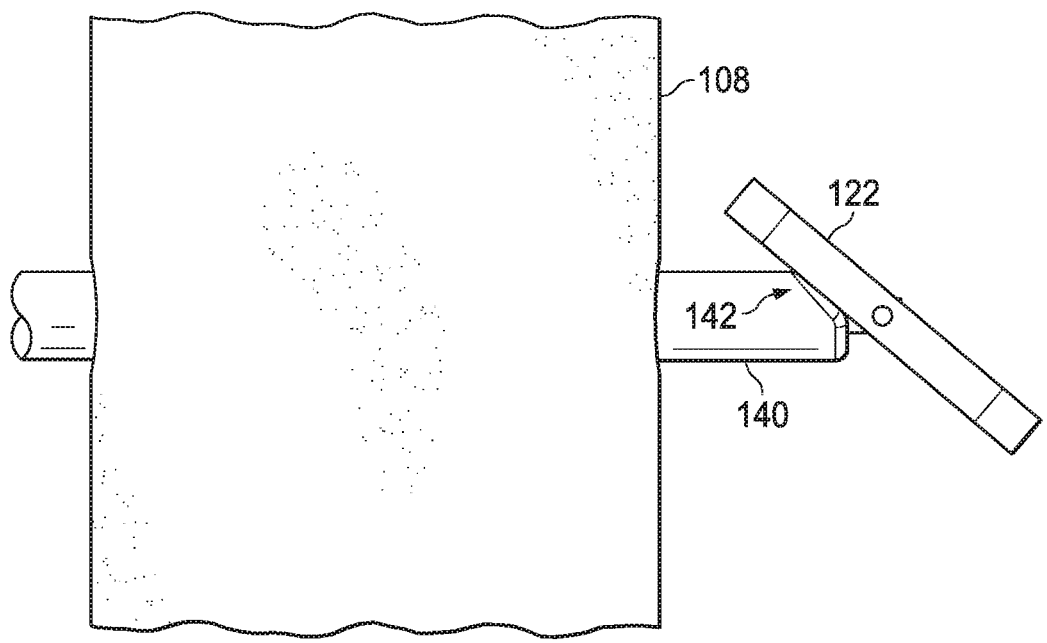
FIG. 10 illustrates a tension washer positioner engaging the tension washer.

FIG. 9 illustrates a side view of the apparatus 100 after the tension washer positioner 140 has been positioned through the fastener hole 104e, and the first and the second holes 114, 116 of the first and the second bones 106, 108. Specifically, the tension washer positioner 140 can be configured to be positioned through the fastener hole 104e, and the first and the second holes 114, 116 of the first and the second bones 106, 108 to adjust an angle of the tension washer 122 with respect to the wire 120, for example, about the pivot point 128. To that end, the tension washer positioner 140 can engage the tension washer 122, and specifically, the angled tip 142 can engage the tension washer 122, as shown in FIG. 10. In some examples, the tension washer positioner 140 adjusts the angle of the tension washer 122 with respect to the wire 120 to be substantially the same as the angle of the angled tip 142 of the tension washer positioner 140.

Figure 11:
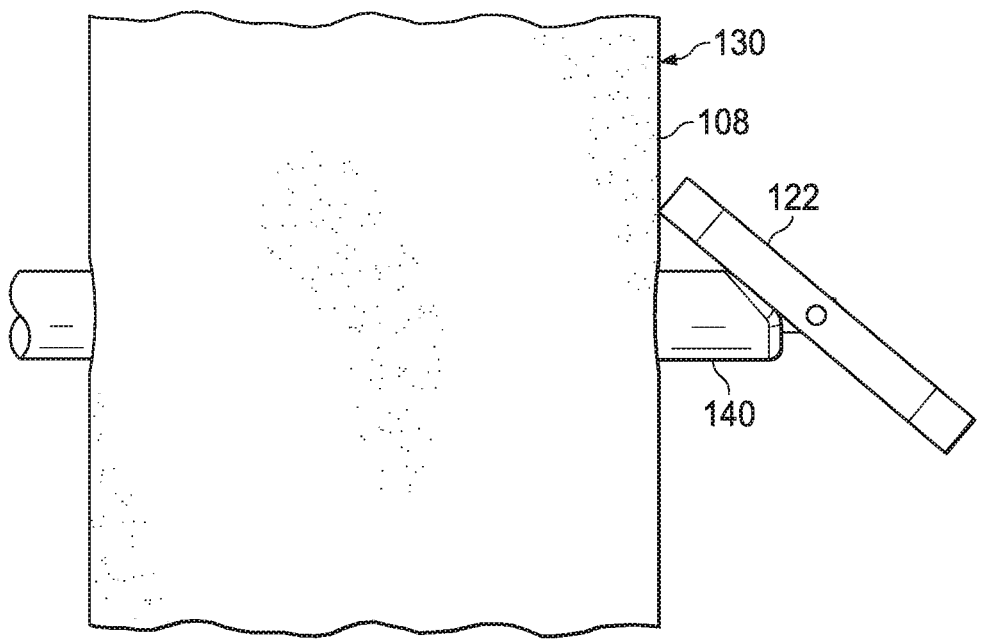
FIG. 11 illustrates a side view of the apparatus after a partial retraction of the tension washer positioner through the fastener hole, and the first and the second holes of the first and the second bones.

FIG. 11 illustrates a side view of the apparatus 100 after a partial retraction of the tension washer positioner 140 through the fastener hole 104e, and the first and the second holes 114, 116 of the first and the second bones 106, 108. As a result, a distance between the surface 130 of the second bone 108 and tension washer 122 can be reduced, for example, such that at least a portion of the tension washer 122 can be in physical contact with the surface 130 of the second bone 108.

Figure 12A:
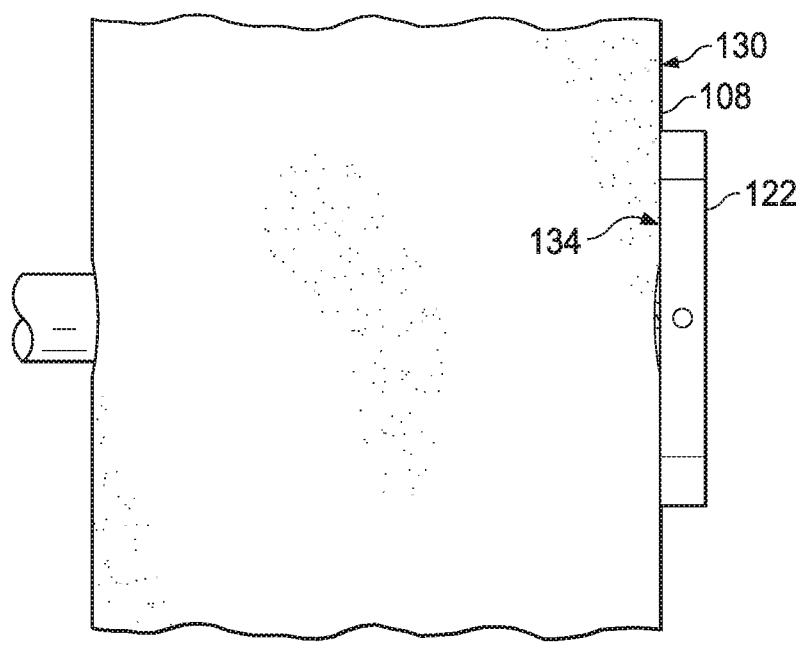
FIGS. 12A, 12B illustrates a side view of the apparatus after a full retraction of the tension washer positioner through the fastener hole, and the first and the second holes of the first and the second bones.
Figure 12B:
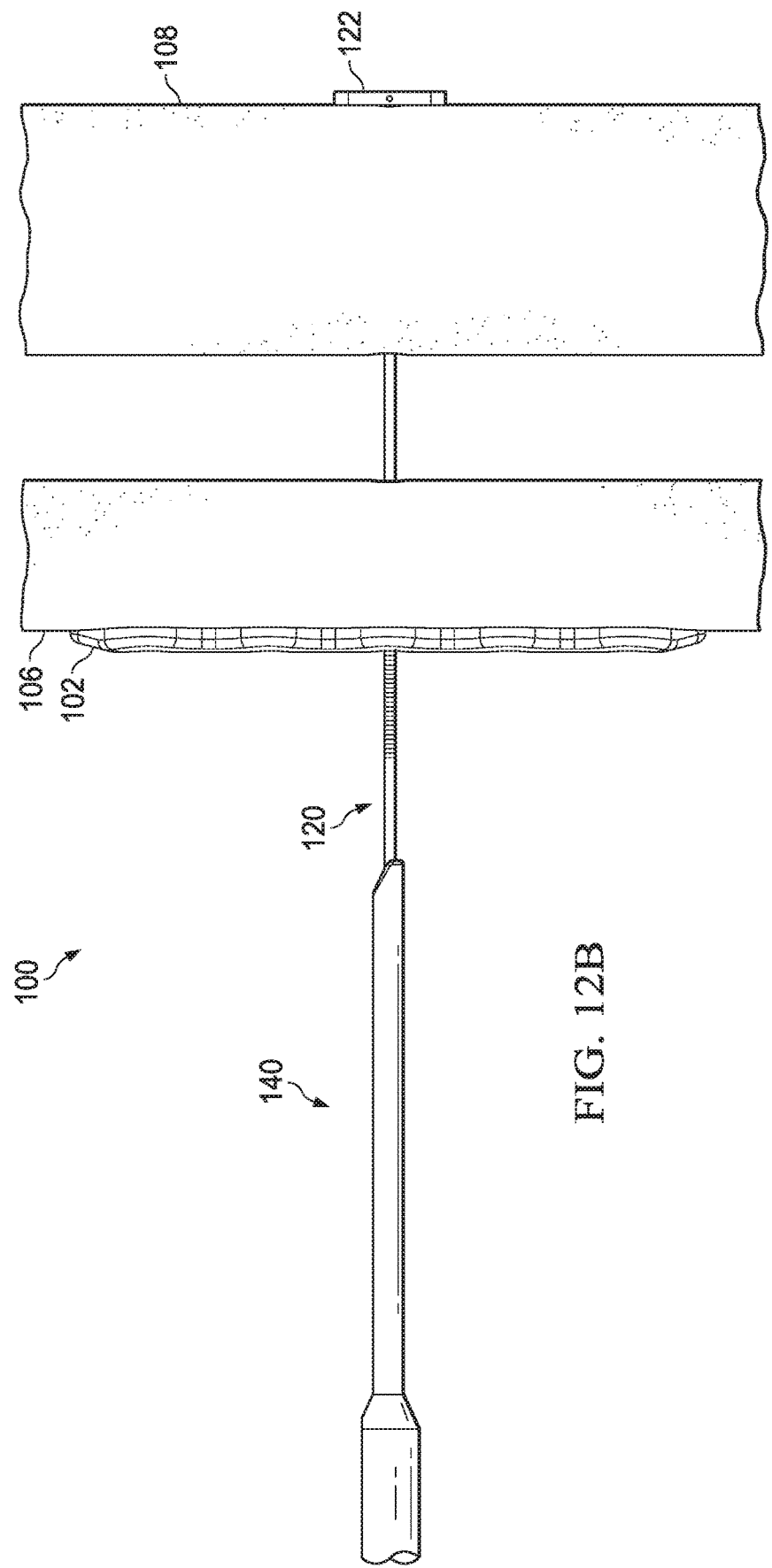

FIG. 12A illustrates a side view of the apparatus 100 after a full retraction of the tension washer positioner 120 through the fastener hole 104e, and the first and the second holes 114, 116 of the first and the second bones 106, 108. Specifically, after the full retraction of the tension washer positioner 120 through the fastener hole 104e, and the first and the second holes 114, 116 of the first and the second bones 106, 108, more clearly shown in FIG. 12B, the first surface 134 of the tension washer 122 can abut the first surface 130 of the second bone 108.

Figure 14:
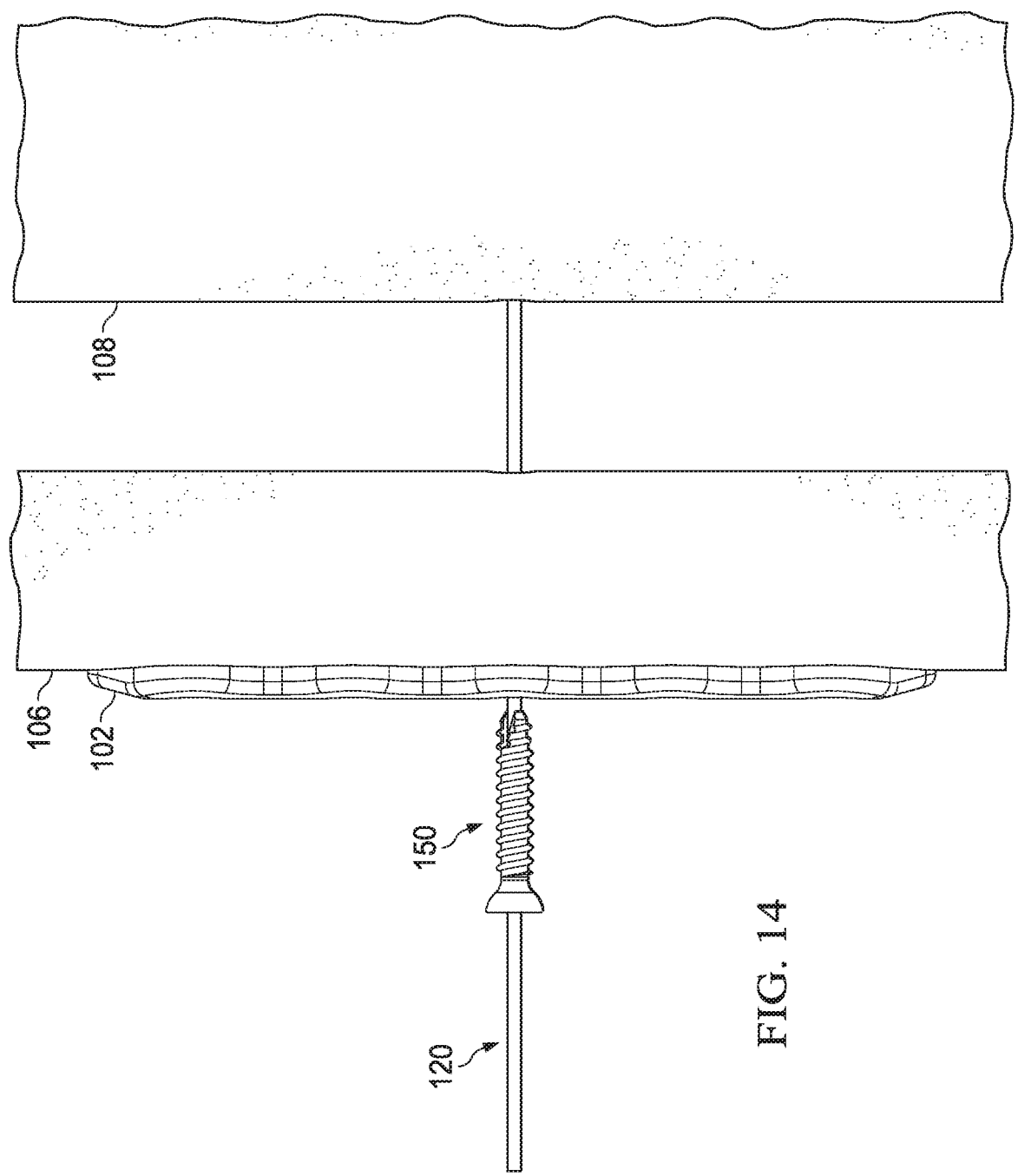
Figure 15:
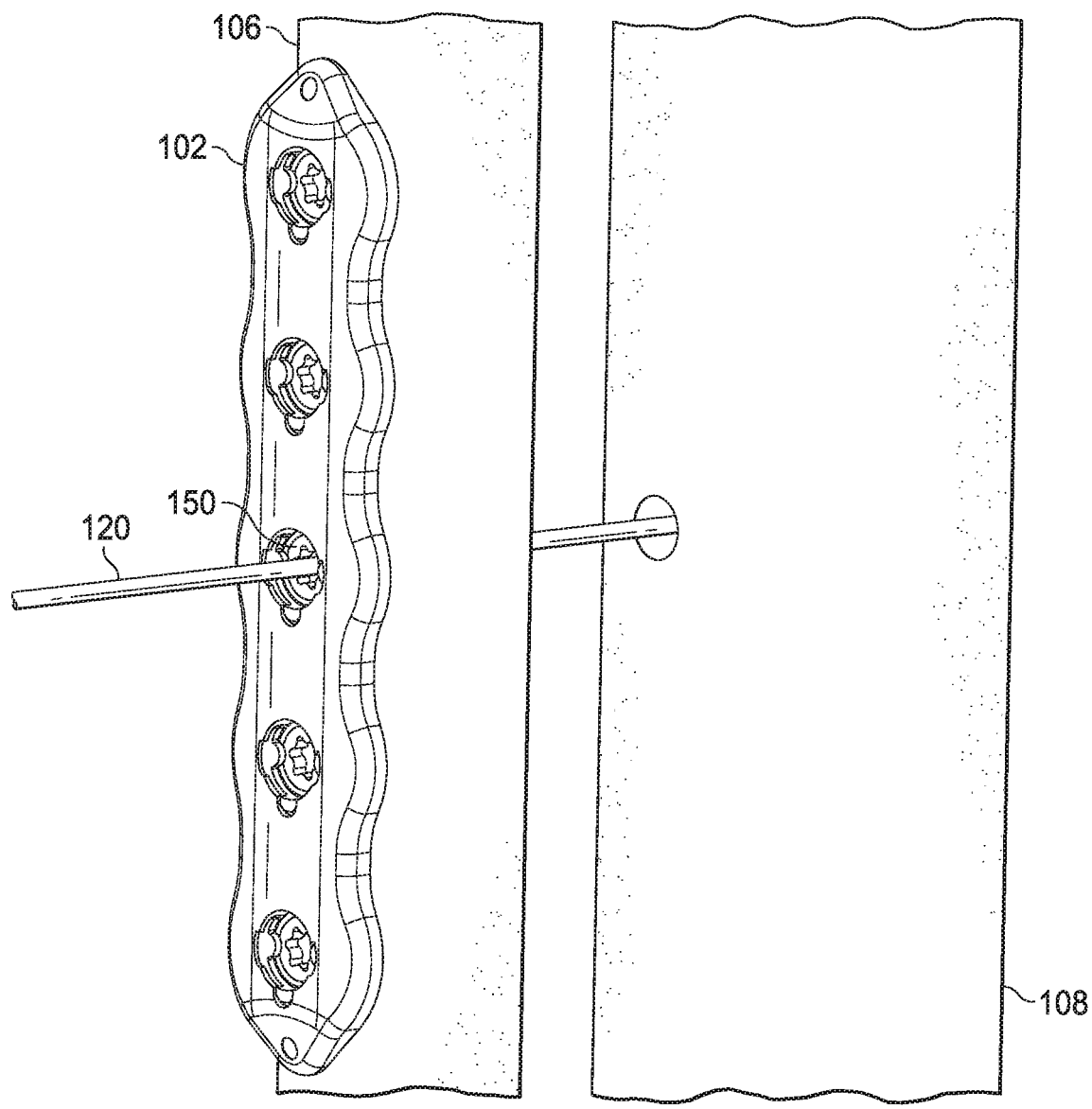
FIG. 15 illustrates a perspective view of the apparatus including a cannulated screw.

FIG. 13 illustrates a side view of the apparatus 100 including a cannulated screw 150. Specifically, the cannulated screw 150 is configured to be inserted over the wire 120 and through the fastener hole 104e, as shown in FIGS. 14, 15. The cannulated screw 150 can be positioned through the fastener hole 104e, and a threaded portion of the cannulated screw 150 can be coupled within the first bone 106.

Figure 16:
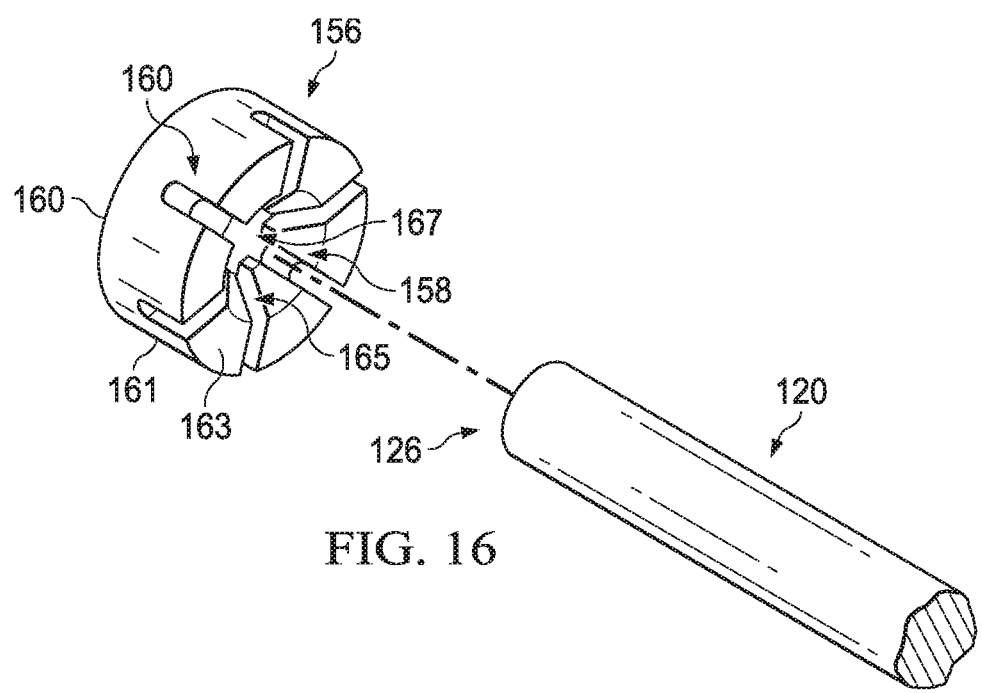
FIG. 16 illustrates a close-up view of a second end of the wire, with the apparatus including a lock washer.

FIG. 16 illustrates a close-up view of the second end 126 of the wire 120, with the apparatus 100 further including a lock washer 156. The lock washer 156 can include an opening 158 with flexible portions 160 surrounding the opening 158. As illustrated, the lock washer 156 can include six flexible portions 160; however, the lock washer 156 can include any number of flexible portions 160. Each of the flexible portions 160 can include a side portion 161, a top portion 163, and a chamfered portion 165. The lock washer 156 can further include a back surface 167 that includes the opening 158, with a gap defined between the back surface 167 and the flexible portions 160.

Figure 17:
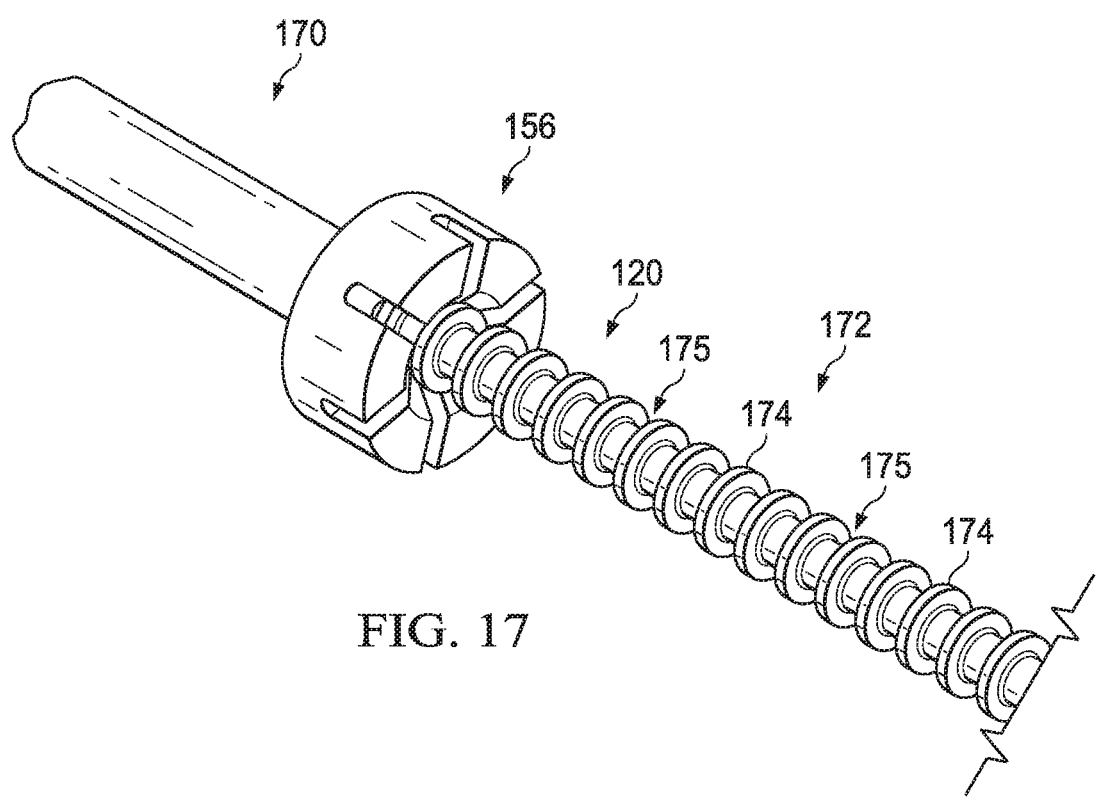
FIG. 17 illustrates the lock washer inserted over the wire.

FIG. 17 illustrates the lock washer 156 configured to be inserted over the wire 120. The wire 120 can include a smooth portion 170 and a toothed portion 172. The smooth portion 170 can be proximate the second end 126 of the wire 120, and the toothed portion 172 can be proximate to the first end 124 of the wire 120. The toothed portion 172 can include a plurality of teeth 174 and a plurality of recesses 175 between adjacent teeth 174. The lock washer 156 can be configured to be inserted over the wire 120. For example, the lock washer 156 can translate along the wire 120 at the smooth portion 170 at the second end 126 of the wire 120 towards the toothed portion 172 at the first end 124 of the wire 120. As the lock washer 156 becomes in contact with the toothed portion 172, the flexible portions 160 of the lock washer 156 can "flex" and increase the size of the opening 158 such that the lock washer 156 can be coupled to a particular tooth 174, and specifically, the tooth 174 that is between the adjacent recesses 175 can be positioned within the gap defined between the back surface 167 and the flexible portions 160 of the lock washer 156. In some examples, the chamfered portion 165 can facilitate flexing of the opening 158 when initial contact between the lock washer 156 and a tooth 174 occurs. That is, the tooth 174 can facilitate applying a force to the chambered portion 165 of the lock washer 156 that increases as the lock washer 156 is translated towards the first end of the wire 120. The toothed portion 172 can minimize and/or prevent, unwanted/undesirable translation of the lock washer 156—for example, in a direction towards the second end 126 of the wire 120. That is, the toothed portion 172 can provide anti-backout of the lock washer 156.

Figure 18:
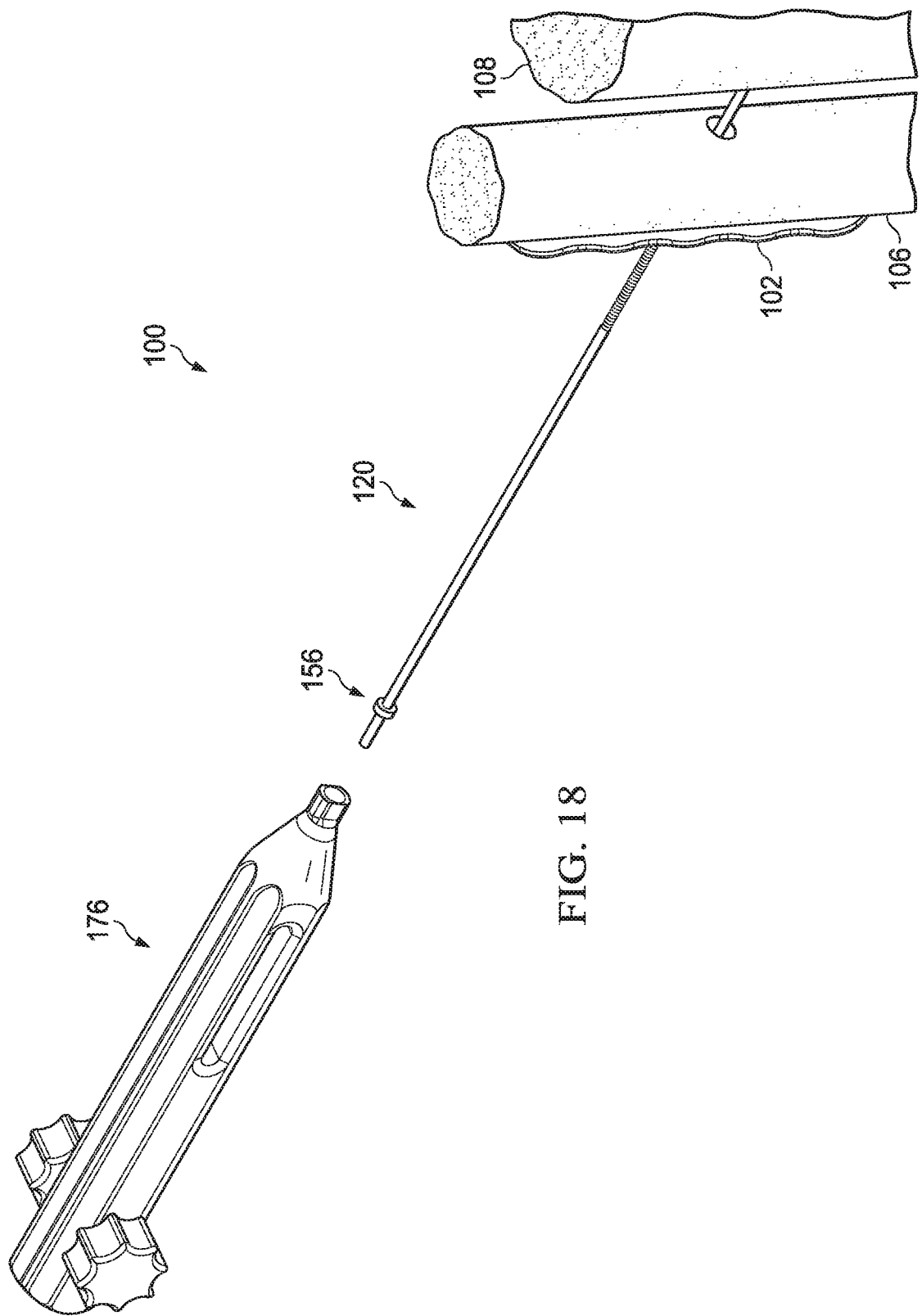
FIG. 18 illustrates a perspective view of the apparatus including a tensioner.
Figure 19:
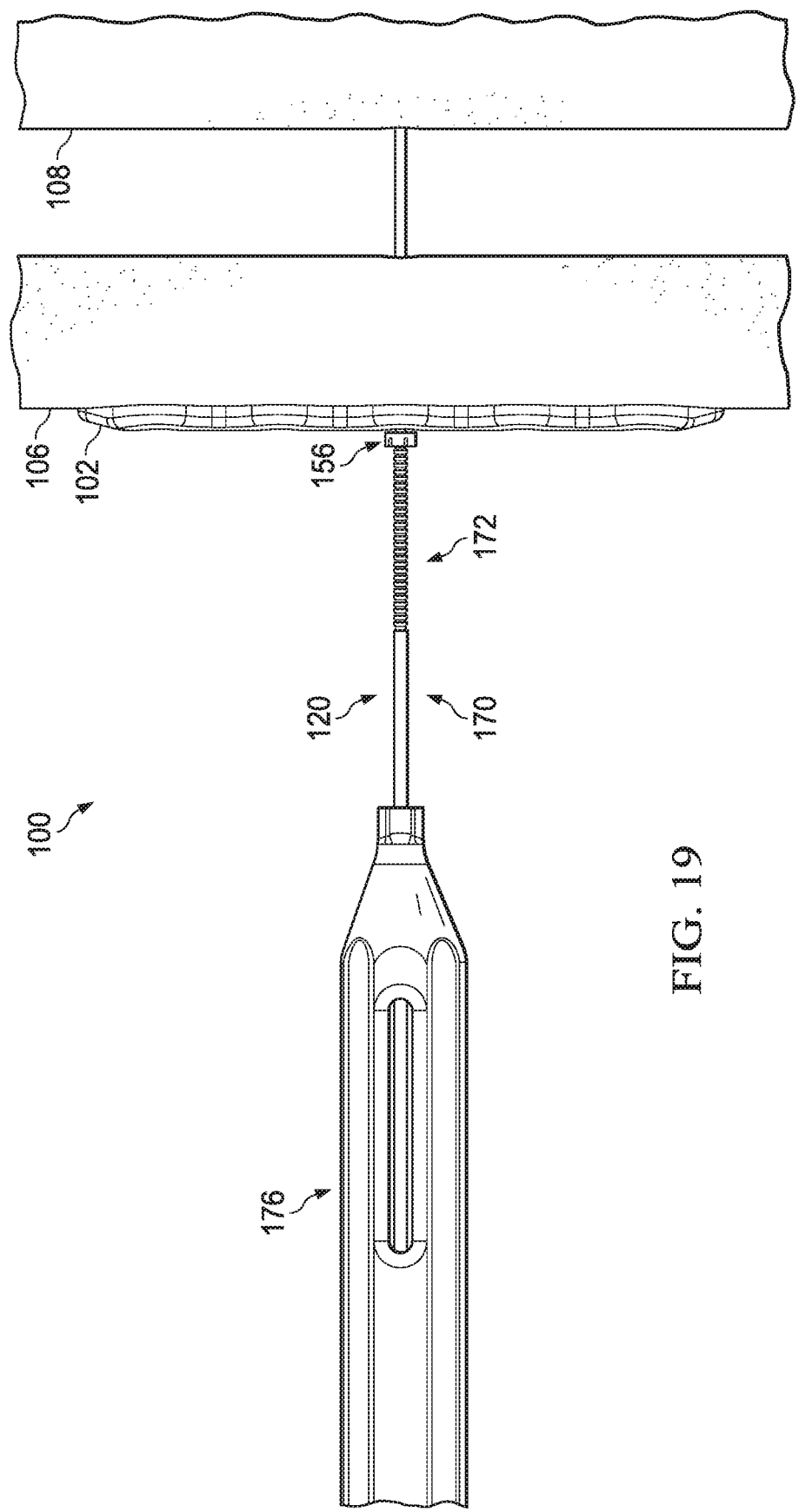
FIGS. 19-20 and 21A illustrate a perspective view of the apparatus including a tensioner.
Figure 20:
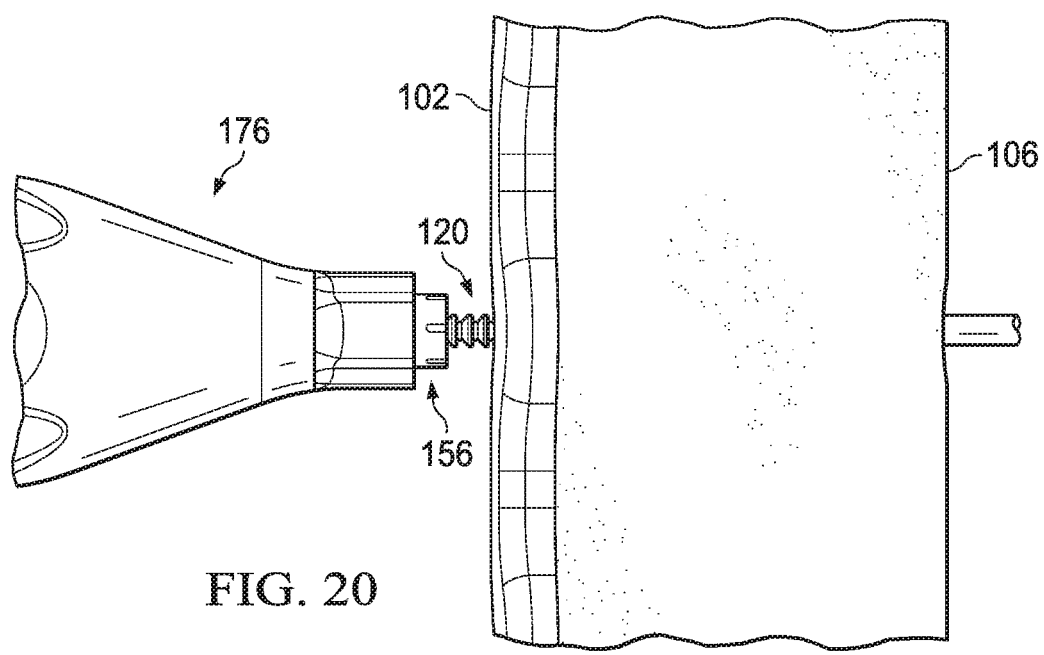
Figure 21A:
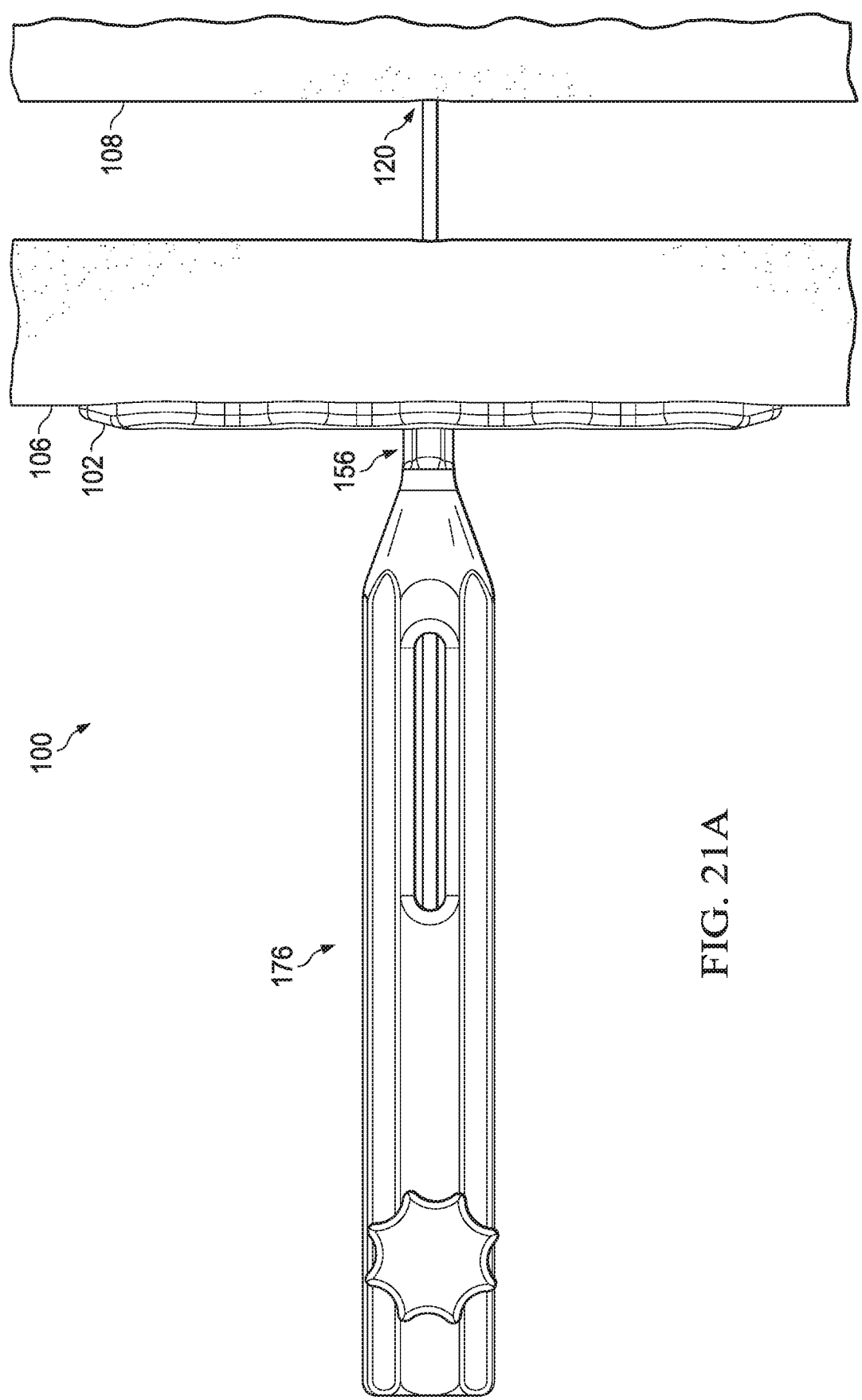
Figure 21B:
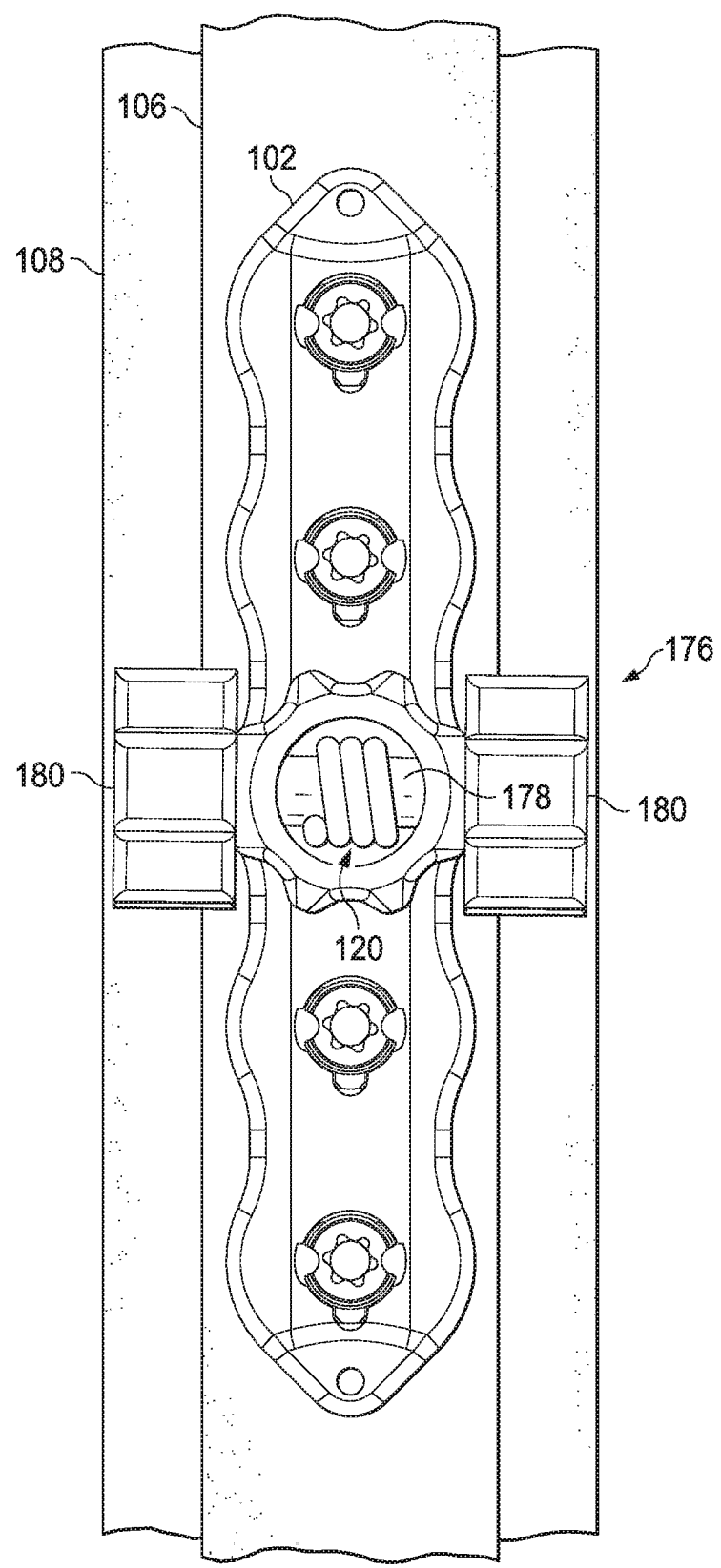
FIG. 21B illustrates a front view of the apparatus including a tensioner

FIG. 18 illustrates a perspective view of the apparatus 100 including a tensioner 176 configured to couple the lock washer 156 to a particular tooth 174 of the toothed portion 172 of the wire 120. Specifically, the tensioner 176 can engage the wire 120 initially at the second end 126 of the wire 120 such that the tensioner 176 is positioned over the wire 120, as shown in FIG. 19. As the tensioner 176 tensions the wire 120, the tensioner 176 can then engage the lock washer 156, as shown in FIG. 20. The tensioner 176 can then position the lock washer 156 such that the lock washer 156 can be coupled to a particular tooth 174 of the toothed portion 172 to obtain a desired tension of the wire 120, as shown in FIG. 21A. FIG. 21B illustrates a front view of the apparatus 100, and specifically, the tensioner 176 wrapping the wire 120 (for example, the smooth portion 170 and/or the toothed portion 172) around a rod 178 via knobs 180 to establish the desired tension on the wire 120. In some examples, the lock washer 156 can be in contact with the cannulated screw 150 when the lock washer 156 is coupled to a particular tooth 174 such that the desired tension of the wire 120 is obtained.

Figure 22:
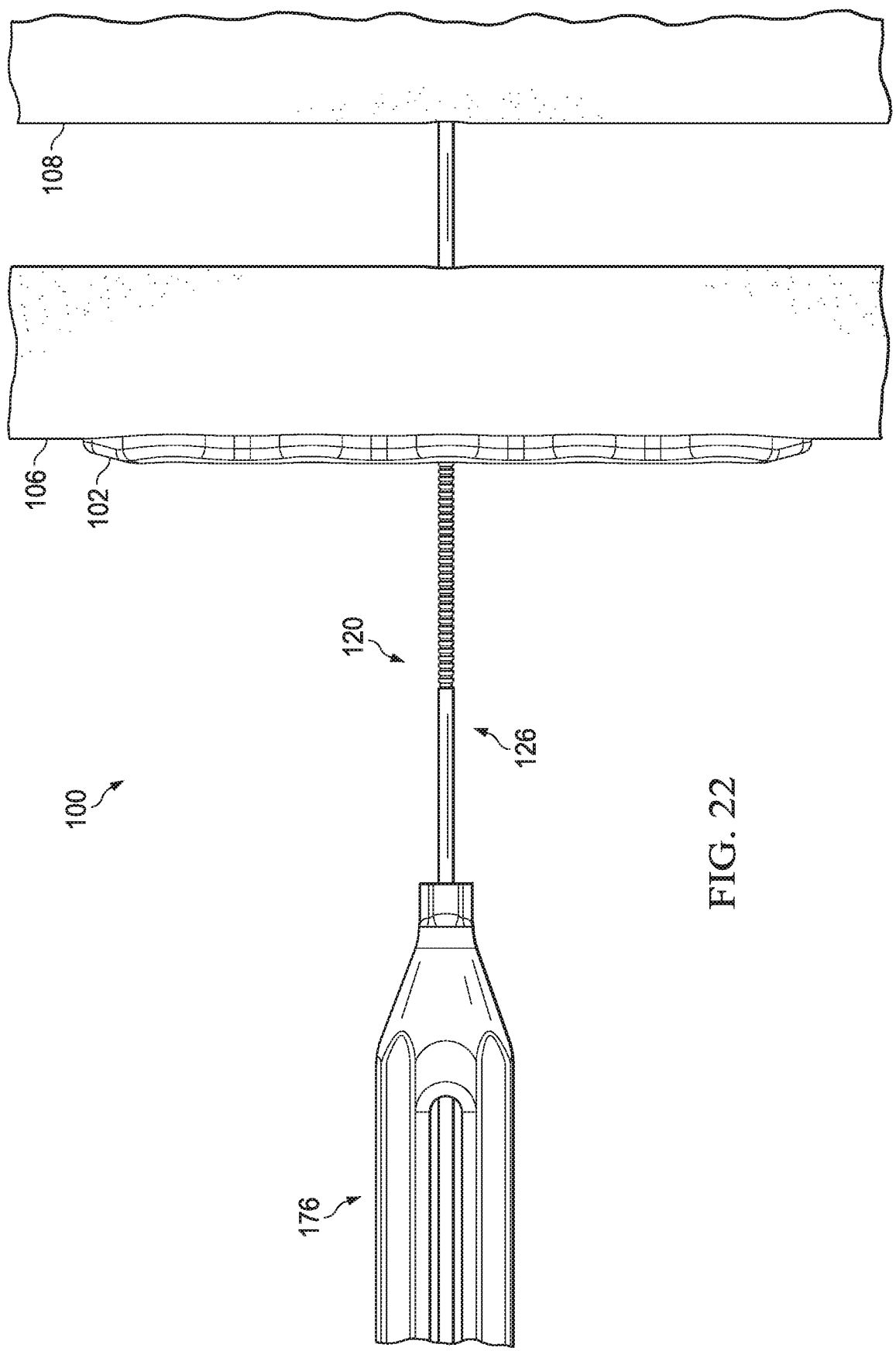
FIG. 22 illustrates a side view of the apparatus after positioning the lock washer between adjacent teeth of a toothed portion of the wire and adjacent the cannulated screw.
Figure 23:
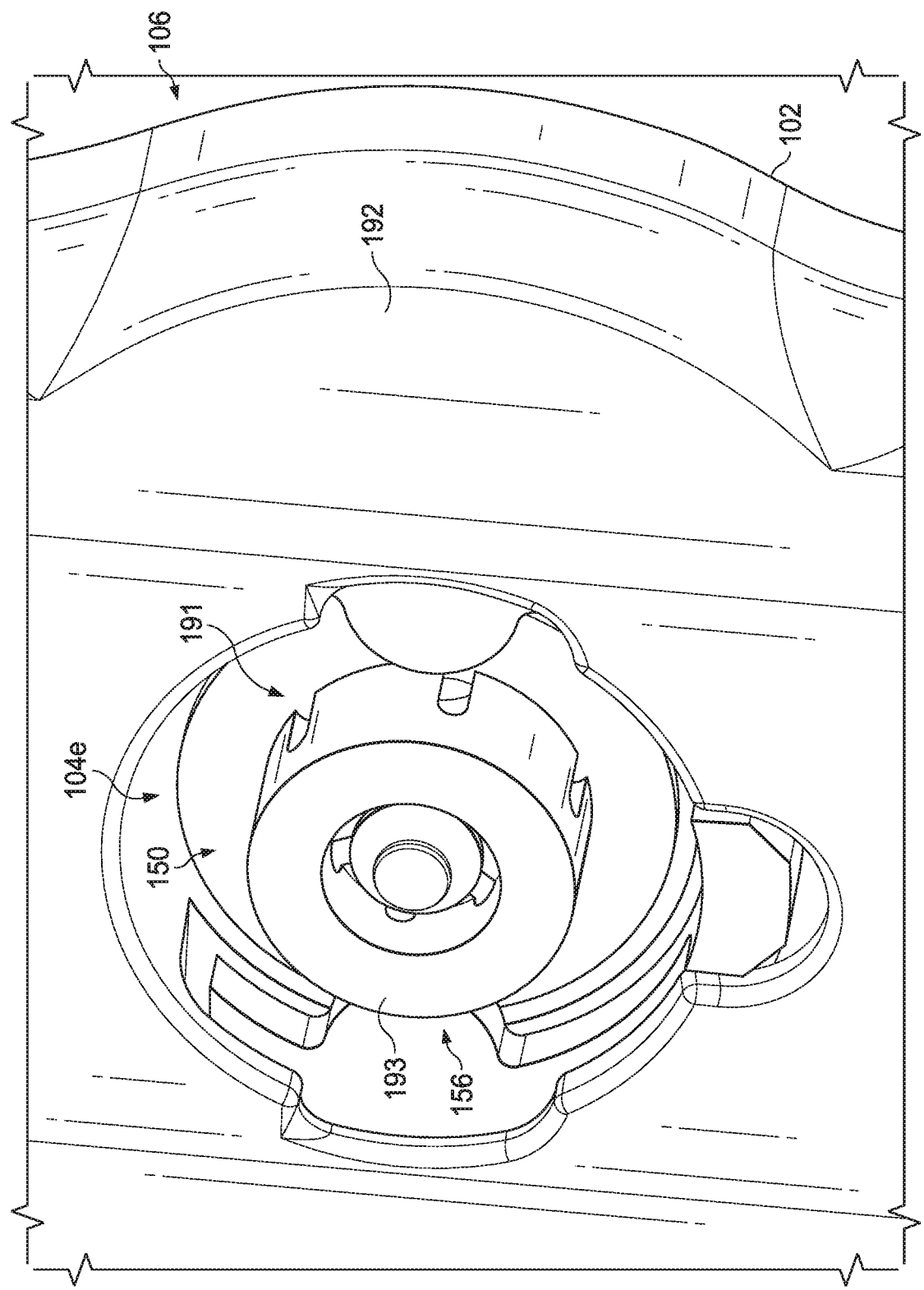
FIG. 23 illustrates the lock washer adjacent the cannulated screw.

FIG. 22 illustrates a side view of the apparatus 100 after coupling the lock washer 156 to a particular tooth 174 of the toothed portion 172 of the wire 120 and adjacent the cannulated screw 150. Specifically, the tensioner 176 can be translated in a direction towards the second end 126 of the wire 120 such that the wire 120 becomes disengaged from the rod 178. Concurrently, the lock washer 156 remains coupled to the particular tooth 174 of the wire 120 and adjacent to the cannulated screw 150, as shown in FIG. 23. Any remaining portion of the wire 120 towards the second end 126 of the wire 120 can be removed. In some examples, the cannulated screw 150 can be recessed within the fastener hole 104e such that a head 191 of the cannulated screw 150 can be spaced apart from a surface 192 of the bone fixation plate 102. To that end, when the lock washer 156 abuts the cannulated screw 150, as shown in FIG. 23, a surface 193 of the lock washer 156 can be flush with the surface 192 of the bone fixation plate 102. In some examples, when the lock washer abuts the cannulated screw 150, the surface 193 of the lock washer 156 can be spaced apart from the surface 192 of the bone fixation plate 102 such that an entirety of the lock washer 156 is positioned within the fastener hole 104e.

Figure 24:
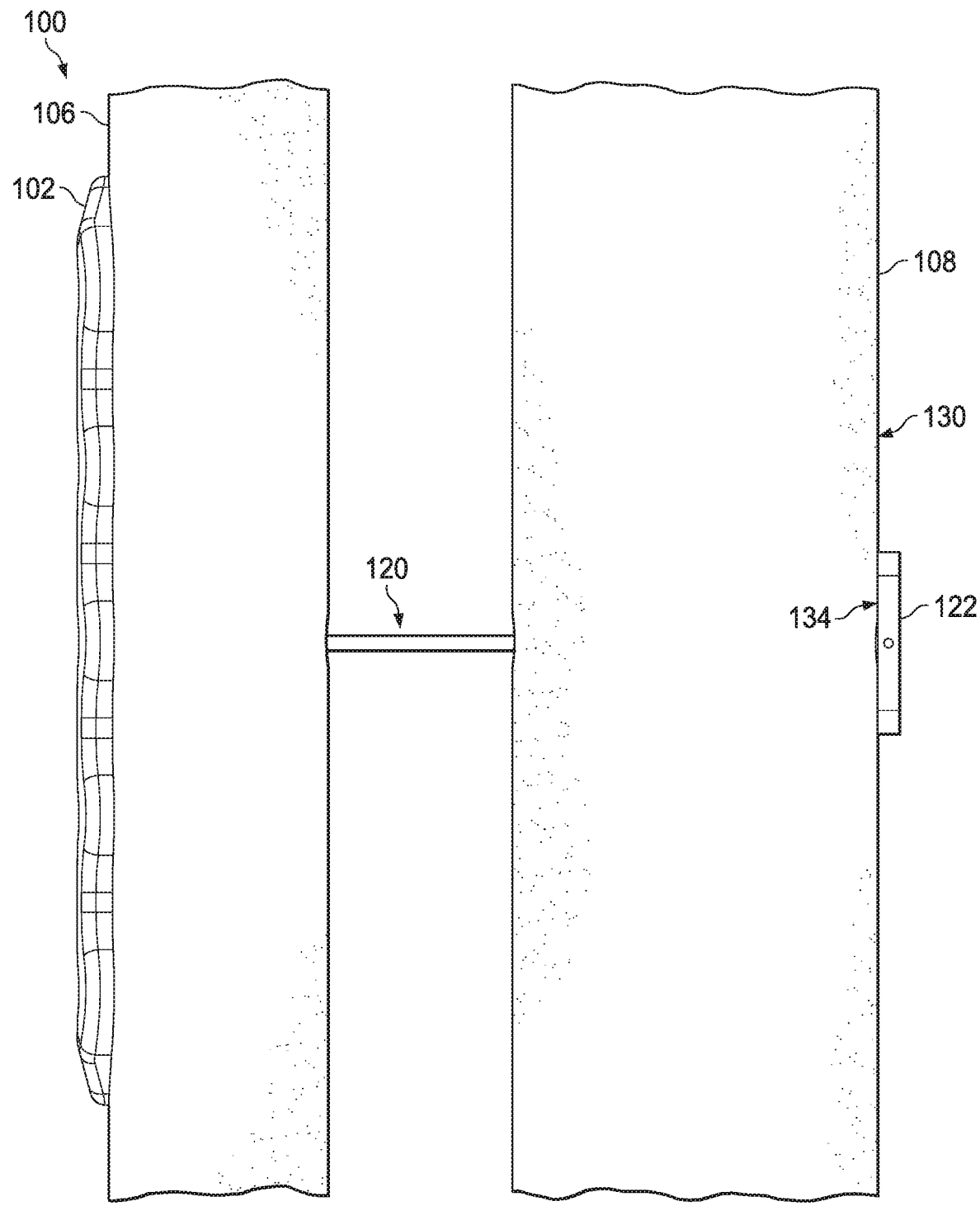
FIG. 24 illustrates a side view of the apparatus after installation of the apparatus for stabilization of the bone fracture site.

FIG. 24 illustrates a side view of the apparatus 100 after installation of apparatus 100 for stabilization of the bone fracture site. Specifically, after lock washer 156 is coupled to a particular tooth 174 such that the desired tension of the wire 120 is obtained, the surface 134 of the tension washer 120 abuts the first surface 130 of the second bone 108 (for example, an at angle of approximately 90 degrees with respect to the wire 120).

Figure 25:
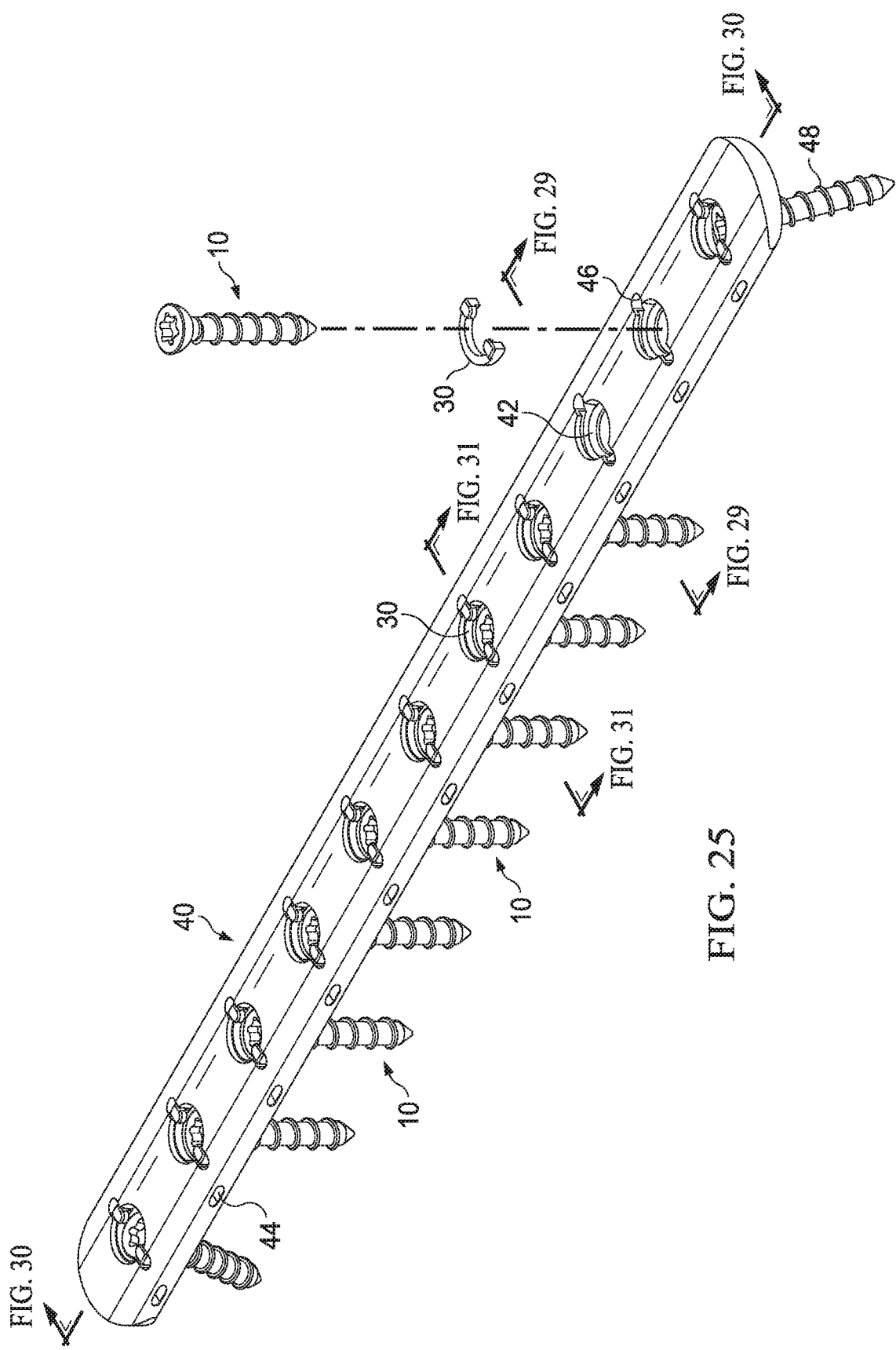
FIG. 25 illustrates a perspective view of the bone fixation plate.

In some examples, the bone fixation plate 102 can be similar to that described in U.S. Pat. No. 10,105,169, hereby incorporated by reference in its entirety. Specifically, FIG. 25 is a perspective view of a bone fixation plate 40, similar to the bone fixation plate 102 of FIG. 1. The plate 40 generally includes a plurality of screw holes, one such screw hole 42 is shown in FIG. 25, similar to the fastener holes 104 of FIG. 1. The screw hole 42 may be threadless with anti-back out feature includes a notch and channel 46 in the sidewall of the hole. The semi-circle-shaped clamp 30 sits within the notch and channel 46. The bone fixation plate 40 may also include openings 44 that allow for visualization of the bone once the plate 40 is inserted. A plurality of orthopedic screws 10, 48 (similar to the fasteners 110 of FIG. 1) can be driven into the bone through the plurality of screw holes 42. While eleven orthopedic screws 10, 48 are illustrated in FIG. 25, those skilled in the art would understand that the bone fixation plate 40 may include more or less than eleven orthopedic screws 10, 48.

Figure 26:
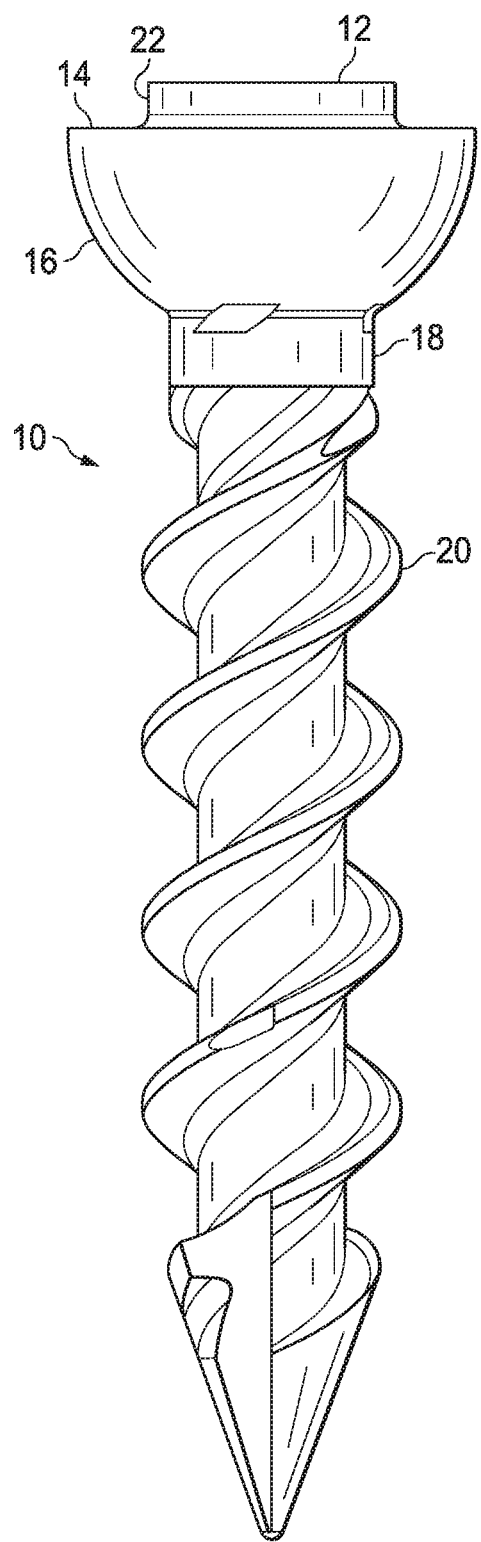
FIG. 26 illustrates a side view of a fastener used in the bone fixation plate

FIG. 26 is a side view illustrating one embodiment of an orthopedic screw used in a bone fixation system with an anti-back out feature. The orthopedic screw 10, similar to the fasteners 110 of FIG. 1) includes a head with an upper recess (not shown) on surface 12, for example, a hex slot, for a driver, a shaft 18 with bone engaging threads 20, and a conical taper 16 at the lower end of the head leading into the shaft 18. The head includes a cylindrical portion 22 with a radius that is less than the radius of the head. As a result, a portion of the clamp 30 (not shown in FIG. 26) can rest on a portion of surface 14.

While the embodiment illustrated in FIG. 26 is a fully threaded cancellous screw, other embodiments may be practiced. As examples, embodiments may be practiced as a partially threaded cancellous screw, a fully threaded cortical screw, a partially threaded cortical screw, a cancellous and cortical screw, and others. Fully threaded screws have threads over substantially the entire length of their shafts, while partially threaded screws have threads over a portion of the length of their shafts, with at least another portion of the length of their shafts unthreaded. A cancellous and cortical screw may have threads of one type along a distal portion of its shaft and threads of another type along a proximal portion of its shaft. The distal portion may be immediately adjacent to the proximal portion, or the distal portion and the proximal portion may be separated from each other, for example, by an unthreaded portion.

Figure 27:
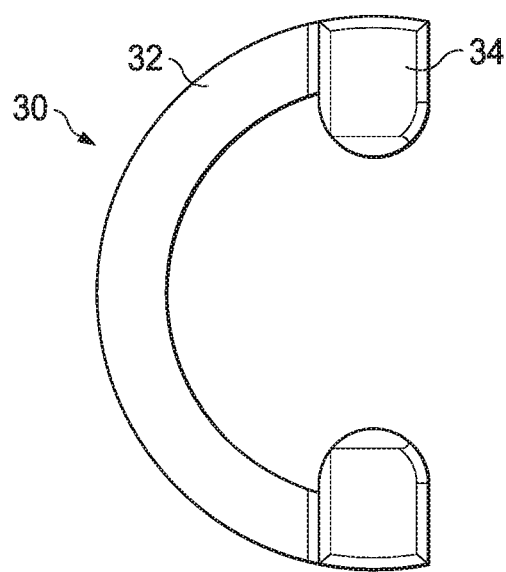
FIG. 27 illustrates a clamp used in the bone fixation plate.
Figure 28:
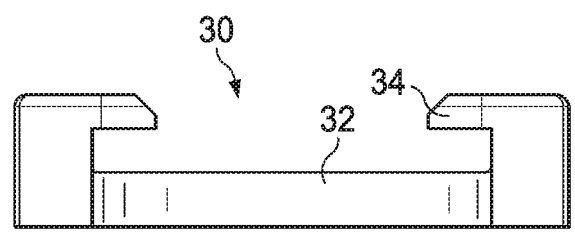
FIG. 28 illustrates an elevation view of the clamp.

FIG. 27 is a top view illustrating one embodiment of a clamp used in a bone fixation system with an anti-back out feature. The clamp 30 includes a substantially semi-circle-shaped washer 32 with two protrusions 34 extending vertically away from the washer 32 and toward the center of the washer 32. FIG. 28 is an elevation view of this embodiment of a clamp 30 of FIG. 27, showing a profile of the washer 32 and protrusions 34.

Figure 29:
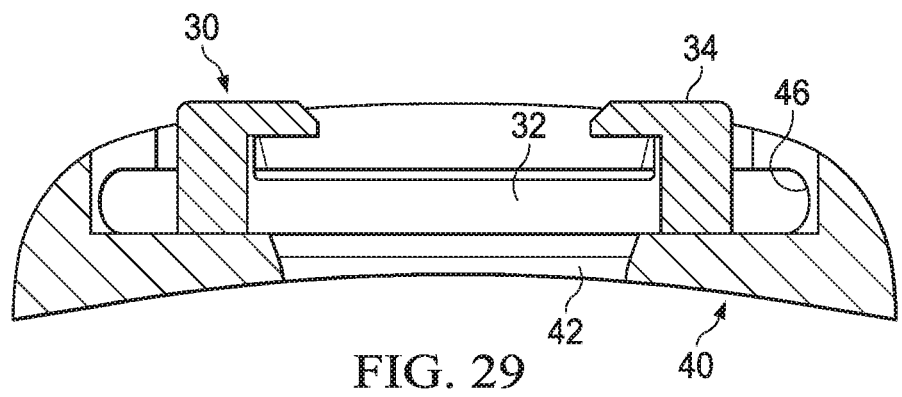
FIGS. 29-31 illustrates cross-sections of the bone fixation plate

FIG. 29 is a cross-section of one embodiment of an orthopedic plate and clamp assembly used in a bone fixation system with an anti-back out feature. Clamp 30 sits within the notch and channel 46 of the hole 42 in the bone fixation plate 40. The washer portion 32 of the clamp 30 sits on the surface of the notch and channel 46. The protrusions 34 of the clamp 30 may be substantially flat with the top surface of the plate 40. The curved structure of the lower surface of the plate 40 complements the natural curved structure of a bone.

Figure 30:
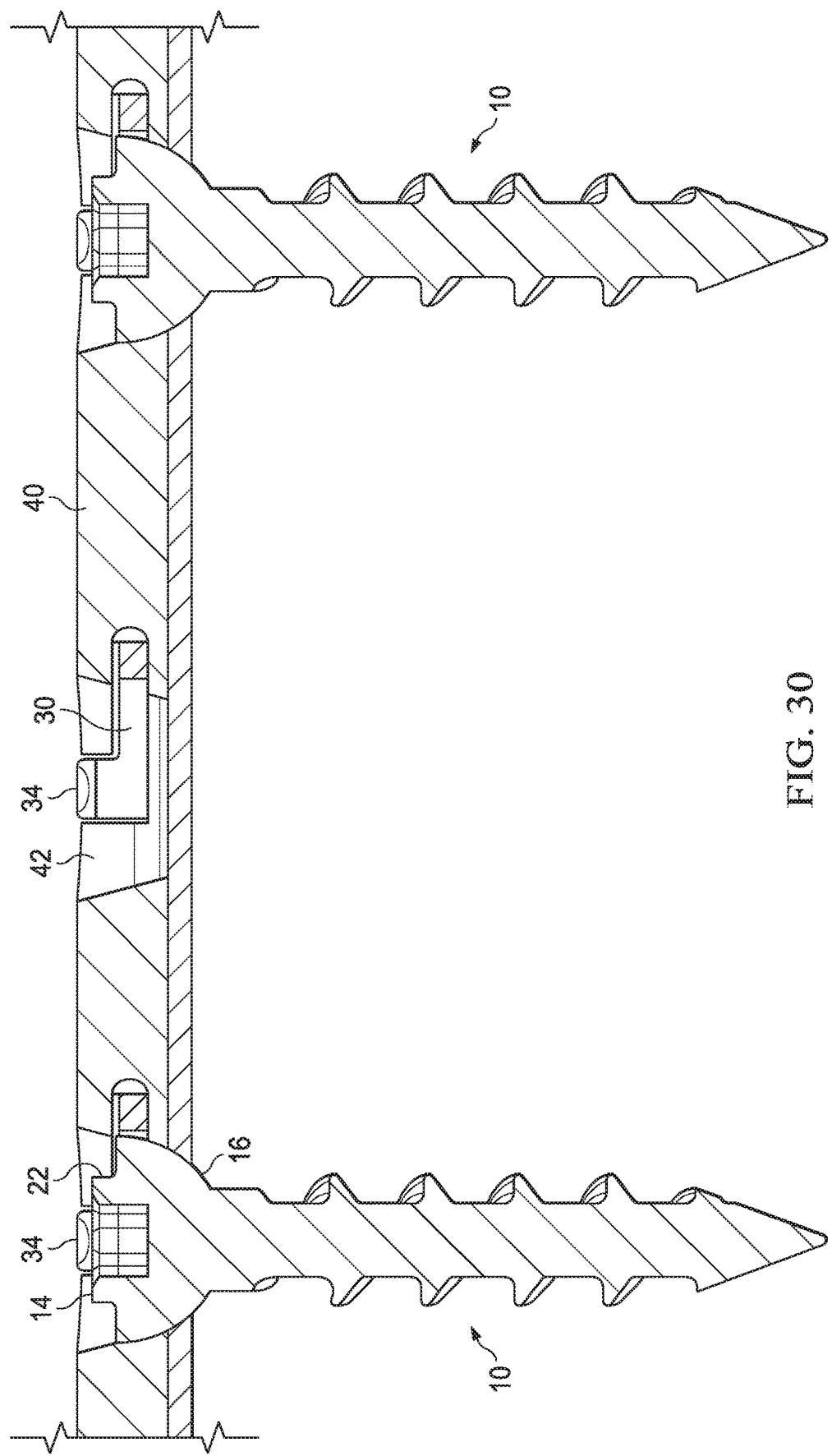

FIG. 30 is a cross-section of one embodiment of an orthopedic plate, clamp, and screw assembly used in a bone fixation system with an anti-back out feature. The head of screws 10 sits within the space defined by the hole 42 in the plate 40, and, as the head is driven toward the bone, the plate is compressed against the bone. The screw 10 can be driven until a desired compression is obtained. The conical taper 16 of the screws 10 sits against the conical taper of the screw holes 42. The conical configuration of both the screw head and the screw hole allow the screws 10 to be inserted either perpendicularly or at an angle into the bone and to provide the desired compression.

The clamp 30, and more specifically the protrusions 34, prevents any loosening or back out of the screw 10 that may occur through micromotion. Due to the conical taper 16 at the lower end of the head of the screw 10, the screw 10 can be inserted into the screw hole 42 and past the clamp 30 without significant resistance from the clamp 30, as the conical taper 16 presents a ramped surface that will partially deflect the clamp 30 into the notch and channel 46 of the hole 42 as the screw is inserted. However, the configuration of the screw 10 with the cylindrical portion 22 that has a radius smaller than that of the rest of the screw head allows the protrusions 34 of the clamp 30 to rest on surface 14 of the screw. With this arrangement, significant interference can be created between the protrusions 34 and the head of the screw 10. As such, the clamp 30 resists unintentional backing out by the screw 10 from the screw hole and can be configured, for example, so that such resistance can be overcome with substantial and intentional manual force applied to the screw.

Figure 31:
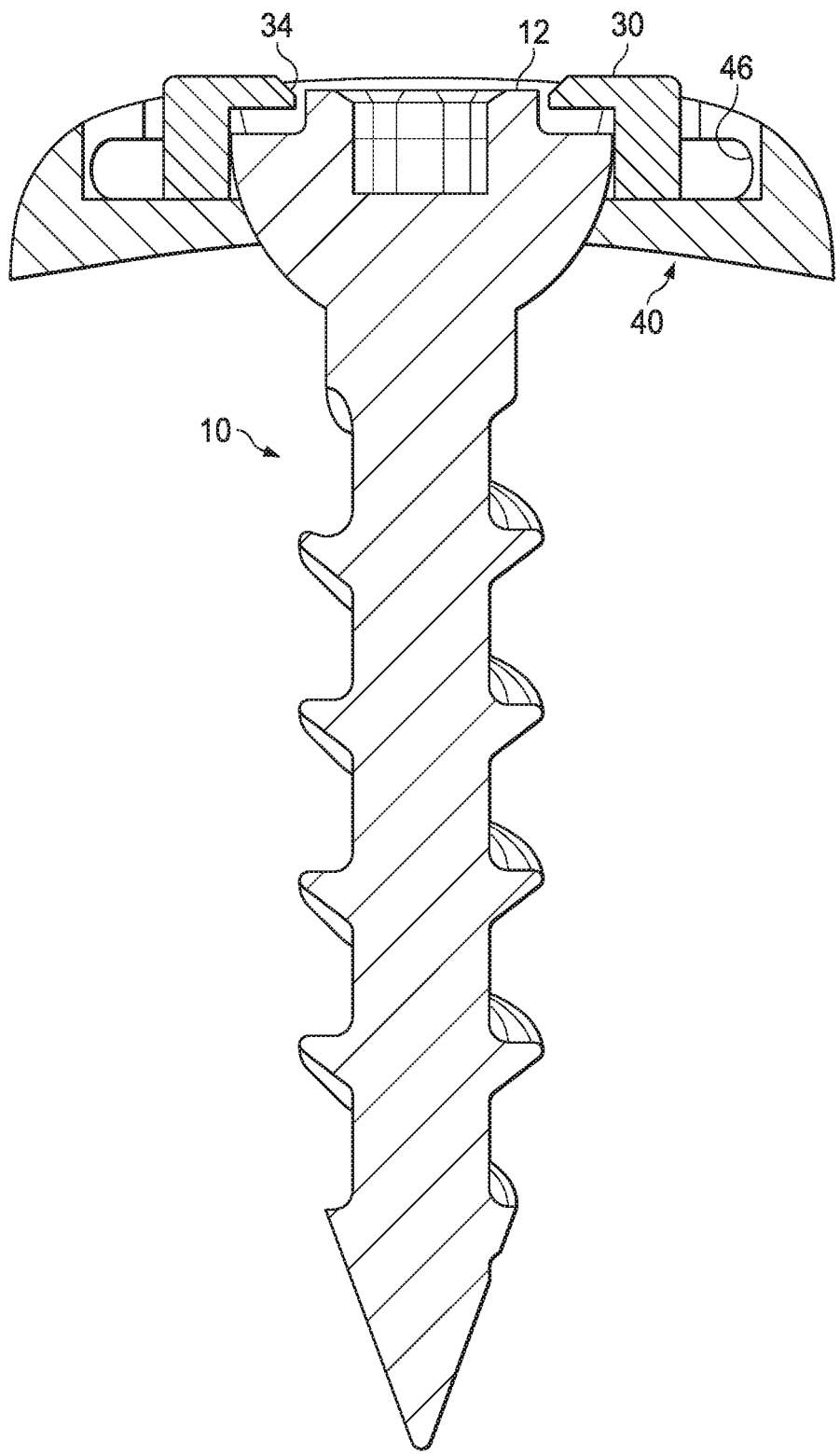

FIG. 31 is a cross-section of one embodiment of an orthopedic plate, clamp, and screw assembly used in a bone fixation system, showing the interference between the protrusions 34 of the clamp 30 and the screw 10. As discussed above, the clamp 30 sits within the notch and channel 46 of the screw hole 42. The protrusions 34 of the clamp prevent the back out of the screw 10. In addition, if screw removal is necessary, the clamp 30 may be positioned within the notch and channel 46 to position the clamp 30 to facilitate screw removal. Moreover, the protrusions 34 of the clamp need not cover surface 12 of the orthopedic screw 10, thus they need not impede access for an instrument to be positioned to remove the screw 10.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, features, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. An apparatus for stabilization of a bone fracture site, the apparatus including:
    a bone fixation plate including a plurality of fastener holes, wherein the bone fixation plate is configured to be coupled to a first bone with one or more fasteners positioned through respective fastener holes of the plurality of fastener holes;
    a wire including i) a smooth portion and ii) a toothed portion;
    a tension washer coupled to a first end of the wire, the tension washer rotatable about the first end of the wire, the wire configured to be positioned through a particular fastener hole of the bone fixation plate and through corresponding holes of the first bone and an adjacent second bone such that the tension washer is positioned proximate a first surface of the second bone opposite a surface of the first bone adjacent the bone fixation plate;
    a cannulated screw configured to be inserted over the wire and through the particular fastener hole to further couple the bone fixation plate to the first bone; and
    a lock washer including a flexible portion with a first lock-washer surface configured to face toward the first bone and a base portion with a second lock-washer surface configured to face away from the first bone, the flexible portion configured to engage the toothed portion of the wire to facilitate translation along the toothed portion in a first direction and to prevent backout along the toothed portion in a second direction opposite of the first direction, the first lock-washer surface of the flexible portion of the lock washer configured to abut a top surface of the cannulated screw to provide tension to the wire to couple the wire to the bone fixation plate, wherein the top surface of the cannulated screw is configured to face away from the first bone.

2. The apparatus of claim 1, further comprising:
a tensioner configured to position the lock washer between the two adjacent recesses of the toothed portion of the wire.

3. The apparatus of claim 1, wherein the one or more fasteners positioned through the respective fastener holes of the plurality of fastener holes are further coupled at least partially within the first bone to couple the bone fixation plate to the first bone.

4. The apparatus of claim 1, further comprising a tension washer positioner including an angled tip, the tension washer positioner configured to be positioned through the particular fastener hole of the bone fixation plate and through the corresponding holes of the first and the second bones to adjust an angle of the tension washer with respect to the wire, wherein the tension washer positioner is cannulated such that the tension washer positioner is configured to be inserted over the wire.

5. The apparatus of claim 1, wherein the tension washer includes a first surface having a length longer than a diameter of the corresponding holes of the first and the second bones, wherein the tension washer is configured to rotate such that when the lock washer is positioned between the two adjacent teeth of the toothed portion of the wire, the first surface of the tension washer abuts the first surface of the second bone.

6. The apparatus of claim 5, wherein the first surface of the tension washer has an angle of approximately 90 degrees with respect to the wire when the first surface of the tension washer is configured to abut the first surface of the second bone.

7. The apparatus of claim 1, wherein a width of the tension washer is less than a diameter of the corresponding holes of the first and the second bones.

8. The apparatus of claim 1, further comprising a tension washer positioner including an angled tip, the tension washer positioner configured to be positioned through the particular fastener hole of the bone fixation plate and through the corresponding holes of the first and the second bones to adjust an angle of the tension washer with respect to the wire, wherein the tension washer positioner is configured to adjust the angle of the tension washer with respect to the tension wire to be substantially the same as an angle of the angled tip of the tension washer positioner.

9. The apparatus of claim 1, wherein the first bone is a tibia, and the second bone is a fibula.

10. The apparatus of claim 1, wherein the tension washer is configured to be rotated with respect to the wire when positioned through the particular fastener hole of the bone fixation plate and the corresponding holes of the first bone.

11. The apparatus of claim 10, wherein the rotation is approximately 15 degrees.

12. The apparatus of claim 1, wherein the toothed portion of the wire includes one or more teeth and one or more recesses between adjacent teeth, wherein when the lock washer is coupled to a particular tooth between adjacent recesses of the toothed portion of the wire, the teeth of the lock washer are configured to prevent movement of the lock washer to a second end of the wire opposite the first end of the wire.

13. The apparatus of claim 1, wherein the lock washer is positioned within the particular fastener hole.

14. The apparatus of claim 1, wherein an upper surface of the lock washer is flush with a surface of the bone fixation plate.

15. An apparatus for stabilization of a bone fracture site, the apparatus including:
a wire configured to be positioned through corresponding holes of a first bone and an adjacent second bone, the wire including a smooth portion and a toothed portion;
a tension washer rotatably coupled to a first end of the wire, and configured to be positioned proximate a first surface of the second bone,
wherein the tension washer includes a first surface having a length longer than a diameter of the corresponding holes of the first and the second bones, wherein the tension washer is configured to rotate about the first end of the wire such that the first surface of the tension washer abuts the first surface of the second bone;
a cannulated screw configured to be inserted over the wire and into to the first bone; and
a lock washer including a flexible portion with a first lock-washer surface configured to face toward the first bone and a base portion with a second lock-washer surface configured to face away from the first bone, the flexible portion configured to engage the toothed portion of the wire to facilitate translation along the toothed portion in a first direction and to prevent backout along the toothed portion in a second direction opposite of the first direction, the first lock-washer surface of the flexible portion of the lock washer configured to abut a top surface of the cannulated screw to provide tension to the wire, wherein the top surface of the cannulated screw is configured to face away from the first bone.

16. The apparatus of claim 15, wherein the tension washer is configured to have a range of rotation about the first end of the wire such that the tension washer forms an angle with respect to the wire.

17. The apparatus of claim 16, wherein the tension washer is configured to have an angle of approximately 90 degrees with respect to the wire when the first surface of the tension washer is placed to abut the first surface of the second bone.

18. The apparatus of claim 16, wherein the tension washer is configured to have an angle of approximately 0 to 15 degrees with respect to the wire when passing through the corresponding holes of the first and the second bones.

19. The apparatus of claim 15, wherein a width of the first surface of the tension washer is less than the length of the first surface of the tension washer.

20. The apparatus of claim 15, wherein the first bone is a tibia, and the second bone is a fibula.

21. The apparatus of claim 15, wherein the tension washer rotatably coupled to the first end of the wire by a pin.

* * * * *